United States Patent [19]

Yeh et al.

[11] Patent Number: 4,560,803

[45] Date of Patent: Dec. 24, 1985

[54] CATALYSTS AND PROCESS FOR OXIDATION OF OLEFINS TO KETONES

[75] Inventors: Chuen Y. Yeh, Edison; Charles Savini, Warren, both of N.J.

[73] Assignee: Exxon Research & Engineering Co., Florham Park, N.J.

[21] Appl. No.: 516,901

[22] Filed: Jul. 25, 1983

Related U.S. Application Data

[63] Continuation-in-part of Ser. No. 420,626, Sep. 21, 1982, abandoned.

[51] Int. Cl.$^4$ ................... C07C 45/34; C07C 45/39
[52] U.S. Cl. ........................... 568/401; 568/402; 568/360; 568/320; 568/69; 568/911
[58] Field of Search ............... 568/365, 408, 401, 360, 568/320, 309, 69, 402

[56] References Cited

U.S. PATENT DOCUMENTS

| | | | |
|---|---|---|---|
| 2,523,686 | 5/1947 | Engel | 260/597 |
| 2,662,921 | 12/1953 | Middleton | 260/604 |
| 3,331,871 | 7/1967 | Ziegler et al. | 260/533 |
| 3,369,049 | 2/1968 | Eden | 260/604 |
| 3,389,965 | 6/1968 | de Ruiter et al. | 23/212 |
| 3,415,737 | 12/1968 | Kluksdahl | 208/139 |
| 3,422,001 | 1/1969 | Kouwenhoven | 208/143 |
| 3,423,331 | 1/1969 | Eden | 252/437 |
| 3,451,946 | 6/1969 | Ziegler et al. | 252/439 |
| 3,487,009 | 12/1969 | Jacobson et al. | 208/138 |
| 3,617,520 | 11/1971 | Kluksdahl | 208/138 |
| 3,649,566 | 3/1972 | Hayes et al. | 252/470 |
| 3,660,271 | 5/1972 | Keith et al. | 208/65 |
| 3,702,827 | 11/1972 | Arganbright | 252/441 |
| 3,773,656 | 11/1973 | Head et al. | 208/111 |
| 3,776,860 | 12/1973 | Rai | 252/455 |
| 3,846,339 | 11/1974 | Blumenthal | 252/438 |
| 3,895,093 | 7/1975 | Weidenbach et al. | 423/213 |
| 4,288,348 | 9/1981 | Schoennagel | 252/441 |
| 4,292,204 | 9/1981 | Mauldin et al. | 252/439 |
| 4,302,358 | 11/1981 | Pellet et al. | 252/441 |
| 4,369,129 | 1/1983 | Mauldin et al. | 252/439 |

FOREIGN PATENT DOCUMENTS

| | | | |
|---|---|---|---|
| 641143 | 12/1963 | Belgium | 568/408 |
| 59179 | 3/1947 | Netherlands | 568/408 |
| 407127 | 10/1932 | United Kingdom | 568/408 |
| 876024 | 1/1958 | United Kingdom | 568/408 |
| 1029175 | 5/1963 | United Kingdom | 508/408 |
| 1054864 | 8/1965 | United Kingdom | 568/408 |
| 52780 | 3/1938 | U.S.S.R. | 568/408 |
| 114924 | 10/1958 | U.S.S.R. | 568/408 |

OTHER PUBLICATIONS

L. Zanderighi et al., *La Chimica E. L'Industria*, vol. 56, No. 12, 815-820, (Dec. 1964).
Y. Moro Oka et al., *J. Catalysis*, vol. 23 183-192 (1971).
W. F. Davenport et al., "Advances in Rhenium Catalysis", *Ind. & Eng. Chem.*, vol. 60, No. 11, pp. 10-19, (Nov. 1968).
H. S. Broadbent et al., *J.A.C.S.*, vol. 76, pp. 1519-1523 (1954).
H. S. Broadbent et al., *J.A.C.S.*, vol. 24, pp. 1847-1854 (1959).
H. S. Broadbent et al., *J.A.C.S.*, vol. 81, pp. 3587-3589, (1959).
H. S. Broadbent et al., *J. Org. Chem.*, vol. 27, pp. 4400-4404, (1962).
R. H. Blom et al., *Hydrocarbon Proc. & Petr. Refin.*, vol. 42, No. 10, pp. 132-134, (Oct. 1963).
R. H. Blom et al., *Ind. & Eng. Chem.*, vol. 54, No. 4, pp. 16-22, (Apr. 1962).
R. Nakamura et al., *J. Molec. Catalysis*, vol. 15, pp. 147-156, (1982).
*J. Org. Chem.*, vol. 24, pp. 1847-1854 (1959).

*Primary Examiner*—James H. Reamer
*Attorney, Agent, or Firm*—J. B. Murray, Jr.

[57] ABSTRACT

An improved process is provided for forming ketones from the corresponding olefins by vapor phase oxidation of the olefin in the presence of molecular oxygen and water vapor employing a heterogeneous catalyst comprising rhenium compounds and complexes, optionally containing at least one metal compound or complex selected from the group consisting of Group VIB metals and Group VIII noble metals, and mixtures thereof. It has been surprisingly found that these catalysts effect the formation of ketones in high selectivities with minimal selectivities to the undesirable carbon dioxide and carbon monoxide by-products.

11 Claims, No Drawings

CATALYSTS AND PROCESS FOR OXIDATION OF OLEFINS TO KETONES

CROSS-REFERENCE TO RELATED APPLICATIONS

This application is a continuation-in-part of our Ser. No. 420,626, filed Sept. 21, 1982 now abandoned, and is related to our applications filed on even date herewith, "Improved Catalytic Process for the Manufacture of Ketones", which is a continuation-in-part of our Ser. Nos. 420,715 and 420,627, both filed Sept. 21, 1982 both now abandoned; "Catalytic Process for the Manufacture of Ketones", which is a continuation-in-part of our Ser. Nos. 420,525, 420,526, 420,648 and 420,716, all filed Sept. 21, 1982 all now abandoned; and "Improved Catalysts and Process for the Conversion of Olefins to Ketones", which is a continuation-in-part of our Ser. No. 420,527, filed Sept. 21, 1982 now abandoned.

BACKGROUND OF THE INVENTION

1. Field of the Invention

This invention generally relates to the catalytic oxidation of olefins to ketones, and more specifically to the formation of ketones by the vapor phase catalytic oxidation of olefins.

2. Description of the Prior Art

British Pat. No. 1,029,175 to Shell describes a vapor phase olefin oxidation process in which olefins are reacted with $O_2$ at temperatures of less than 350° C. in the presence of water vapor and a halogen, using a supported Group VIII noble metal catalyst containing either an Fe, Ni, Co or Group I or VII transition metal compound, optionally together with an alkali metal compound or one or more transition metal compounds of Groups III–VI. While propylene oxidation is said to give acetone as the main reaction product, such halide-containing systems have severe disadvantages such as the high corrosivity of these systems.

British Pat. No. 876,024 (1961) forms aldehydes and ketones by contacting the corresponding olefin and oxygen over a catalyst containing a strong acid compound of a transition metal of the fifth to eighth group or first sub-group of the Periodic System, in the presence of steam. Illustrated are catalyst compounds containing anions derived from such strong acids as HCl and HBr.

U.S. Pat. No. 2,662,921 (1953) oxidatively converts olefins into unsaturated ketones (e.g., propylene to acrolein) using a catalyst containing at least one oxide of Te and Re, and in the presence of free $O_2$. Other patents disclosing catalyst systems for forming unsaturated such aldehydes using Re-containing catalysts are: U.S. Pat. Nos. 3,331,871 and 3,451,946 to C. E. Ziegler, et al. (feed=propylene and $O_2$ and optionally, water vapor, over catalyst containing $CoMoO_4$, $TeO_2$ and a Re compound, to form a mixture of acrolein and acrylic acid); and U.S. Pat. Nos. 3,369,049 and 3,423,331 to J. S. Eden et al. (acrolein or methacrolein prepared from propylene or isobutylene and $O_2$, with or without water vapor, over a catalyst comprising a mixture of certain Cu, Te and Re compounds).

An early patent (U.S. Pat. No. 2,523,686 to W. F. Engel of Shell) employs catalysts containing (1) an oxide of a metal of Groups II, III, IV or VI of the Periodic Table and (2) a metal or partially reduced oxide of a metal of Group IB, Group VII or Group VIII of the Periodic Table, and prepares saturated open-ended ketones from olefins of at least three carbon atoms per molecule in a vapor phase process in the presence of steam and under defined conditions. The U.S. patent indicates that Mn is preferred over other Group VII metals (Re and Ti) in the patentee's catalysts. The catalysts are prepared by partial reduction of the metal oxide with $H_2$. Dutch Pat. No. 59,179, also to W. F. Engel, relates to similar catalyst systems. Neither patent contains any working example to a Re catalyst system.

U.S. Pat. No. 3,389,965 to Shell discloses a process for producing $H_2$ by steam reforming of hydrocarbon petroleum fractions over a Re-containing catalyst at 400° to 600° C. or higher, which, of course, results in the formation of $CO_2$ and CO in very large amounts. The patent, however, does not relate to the selective, partial oxidation of olefins or alcohols or to the production of ketones and other oxygenated products.

Manganese, another Group VIIB metal, has been investigated in various catalyst systems as a catalyst promoter. L. Zanderighi, et al., *La Chimica E L'Industria*, vol. 56, n. 12, 815–820 (Dec., 1964) report, for a series of propylene-oxidations to a product mixture of acrolein, acetone, acetaldehyde, propylene oxide and methanol, using various tungstates ($WO_4^-$), of a series of cations, that the reactivities of the tested cations was: $Cu>>Bi>Pb>Fe>Tl>Mn$. Y. Moro Oka, et al., *J. Catalysis*, vol. 23, 183–192 (1971) indicates that no oxygenated products other than carbon oxides were found in propylene oxidation over a $Mn_2O_3$—$MoO_3$ catalyst.

W. H. Davenport et al., "Advances in Rhenium Catalysis", *Ind. & Eng. Chem.*, vol. 60, no. 11, pp. 10–19 (Nov. 1968) states that the chemical and catalytic properties of Re differ considerably from Mn. For example, whereas metallic Mn is highly reactive, slowly decomposes water and reacts with dilute acids, Re metal is relatively inert and does not react with water or nonoxidizing acids. Re catalysts are said to be highly selective hydrogenation catalysts. In the presence of $H_2$, supported or unsupported Re metal preferentially catalyzes the attack by $H_2$ upon carbonyl functions over olefinic bonds, while Re oxides catalyze the saturation of C=C bonds first.

Re-containing hydrogenation catalysts are also disclosed in British Pat. No. 407,127 (1934); H. S. Broadbent et al., *J.A.C.S.*, vol. 76, pp. 1519–1523 (1954); H. S. Broadbent et al., "*J. Org. Chem.*, Volume 24, pp. 1847–1854 (1959) H. S. Broadbent et al., *J.A.C.S.*, vol. 81, pp. 3587–3589 (1959); H. S. Broadbent et al., *J. Org. Chem.*, vol. 27, pp. 4400–4404 (1962).

R. H. Blom et al., *Hydrocarbon Proc. & Petr. Refine*, vol. 43, no. 10, pp. 132–134 (Oct. 1963) and R. H. Blom et al., *Ind. & Eng. Chem.*, vol. 54, no. 4, pp. 16–22 (April 1962) discuss the use of certain Re catalysts in the dehydrogenation of alcohols to aldehydes and ketones.

Rhenium dehydrogenation catalysts are prepared in U.S.S.R. Pat. No. 52,780 (1938), as abstracted at 34 *Chem. Abs.* 5467-7; and U.S.S.R. Pat. No. 114,924 (1958), as abstracted at 53 *Chem. Abs.* 10596f.

Belgian Pat. No. 641,143 (1963) added Re to a supported catalyst containing Fe—Sb oxide on silica to catalyze the oxidation of propylene to acrolein.

British Pat. No. 1,038,262 (1966) employed Re oxides to promote supported and unsupported Co and Ni molybdates and Cu phosphate to oxidize propylene to acrolein or acrylic acid.

British Pat. No. 1,054,864 (1967) obtained significant disproportion of 1-butene (62% butene conversion) over 23% $Re_2O_7$ on $Al_2O_3$ (at 150° C., atm. pressure) and a space velocity of 1600, to a 62% butene conversion chiefly to propylene and pentene, with some by-product $C_2$ and $C_6$ olefins. Olefin methathesis reactions using $O_2$ and Re oxide/alumina catalysts are discussed in R. Nakamura, et al., *J. Molec. Catalysis,* vol. 15, pp. 147–156 (1982) (which is not admitted herein to be prior art to our invention).

SUMMARY OF THE INVENTION

According to the improved process of this invention, ketones are formed in high selectivities in the vapor phase partial oxidation of olefins in the presence of water vapor and molecular oxygen over a heterogeneous catalyst comprising rhenium and complexes or compounds thereof, which can be optionally supported with at least one metal selected from the group consisting of Group VIB and Group VIII noble metals and compounds or complexes thereof.

It has been surprisingly found that the catalysts of this invention can provide ketones in significantly improved selectivities, and these results are particularly surprising in view of the prior art teachings regarding the oxidation of propylene over certain manganese catalysts, a metal which also occupies a Group VIIB metal position in the Periodic Table, as does rhenium itself.

It has been further found that the catalysts of this invention can effect the above results without the formation of substantial amounts of hydrogenation by-products, such as butane from butene feeds, and such olefin saturation by-products have been detected in the gaseous effluents from the process of this invention in only minimal amounts, if at all.

DETAILED DESCRIPTION OF THE INVENTION

Catalyst

The catalysts of this invention comprise Re, preferably in a supported form. The Re can be present in a variety of forms including a Re compound or complex. When present as a Re compound, the metal can be chemically combined with an inorganic anion such as oxygen, sulfur and halide (Br, Cl, I or F). Preferred are non-halide Re catalysts such as those selected from the group consisting of Re oxide, Re sulfide and mixtures thereof. Particularly preferred Re oxide and sulfides are $Re_2O_3$, $ReO_2$, $ReO_3$, $Re_2O_5$, $Re_2O_7$, $Re_2S_7$, $ReS_2$, $ReS_3$ and $Re_2S_5$.

The Re catalyst can optionally contain as a promoter a member selected from the group consisting of a metal or metal compound or complex of a Group VI metal, a Group VIII noble metals or a mixture thereof. Thus, also suitable as catalyst for the vapor phase process of this invention are Re catalysts containing, as the metal or as compounds or complexes thereof, any one of Cr, Mo, W, Ru, Rh, Pd, Os, Ir and Pt. These additional elemental components of the catalyst can be present as the metals themselves (that is, in the reduced state) or as compounds or complexes thereof, or as mixtures of the foregoing. Any of the inorganic anions discussed above with respect to Re are also suitable as anions with which the additional Group VIB or Group VIII noble metals can be combined. As with the Re component, the Group VIB and/or noble metal will be preferably present in the non-halide form, e.g., an oxide or sulfide. Illustrative of suitable bimetallic catalysts of this invention are Re—Mo, Re—W, Re—Rh, Re—Cr, Re—Pd, Re—Pt, Re—Ir, Re—Ru and Re—Os oxides and sulfides, and mixtures of the foregoing. Illustrative trimetallic catalysts of this invention are oxides and sulfides of Re—Cr—Ru, Re—Mo—Rh, Re—W—Rh, Re—Mo—Pd, Re—Mo—Os, Re—Mo—Pt, Re—W—Pd, Re—W—Os and mixtures of the foregoing. Especially preferred are oxides and sulfides of Rh—Re—Mo, Pd—Re—Mo and Rh—Re—W.

The Re is preferably present in the promoted catalysts of this invention in a Re:promoter metal weight:weight ratio of from about 0.0001:1 to 10:1, and more preferably from about 0.01:1 to 1:1. Thus, Re—Mo catalyst will preferably contain from about 0.0001 to 10 parts by weight of Re per part by weight of Mo, and more preferably from about 0.01 to 1 part by weight of Re per part by weight of Mo. Similarly, in Re—Rh—Mo catalysts, the weight ratio of Re:(Rh+Mo) will preferably range from about 0.0001 to 10:1, and more preferably from about 0.01 to 1:1.

The catalysts which are used in the process of the present invention are solids which can be prepared by any of the methods known in the art. Furthermore, they can be employed in any suitable form, for example, as granules, pellets, powders and the like, and they can be either used as such or supported (as is preferred) on or admixed with an inert material, such as alumina, silica, silica-alumina, zeolites, pumice, any of the activated earths, kieselguhr, clays and the like. The preferred support for the catalyst of this invention is alumina, and most preferably gamma-alumina.

Preferred supported bimetallic Re catalysts of this invention are those containing from about 0.1 to 10 wt.% Re together with from about 1 to 30 wt.% of a Group VIB metal (e.g., Mo or W), and more preferably those containing from about 1 to 5 wt.% Re, together with from about 3 to 15 wt.% of a Group VIB metal (e.g., Mo or W), calculated as wt.% of the indicated metals based on the total weight of the supported catalyst. Preferred supported trimetallic Re catalysts of this invention are those containing (based on the total weight of the supported catalyst) from about 0.001 to 5 wt.% of a Group VIII noble metal (e.g., Rh, Pd, Pt or Ru), from about 0.1 to 10 wt.% Re together with from about 1–30 wt.% Mo, and, more preferably, those containing from about 0.1 to 1.0 wt.% of a Group VIII noble metal (e.g., Rh, Pd, Pt or Ru), from about 1 to 5 wt.% Re together with from about 3 to 15 wt.% of a Group VIB metal (e.g., Mo or W), calculated as wt.% of the indicated metals based on the total weight of the supported catalyst. Preferred supported trimetallic Re catalysts of this invention are those containing (based on the total weight of the supported catalyst) from about 0.001 to 5 wt.% Rh, from about 0.1 to 10 wt.% Re together with from about 1–30 wt.% Mo, and, more preferably, those containing from about 0.1–1.0 wt.% Rh, from about 1 to 5 wt.% Re, together with from about 3 to 15 wt.% Mo.

Most preferably, the catalyst composition ranges from 1 to 30 wt.% of catalyst metals in relation to the total weight of the supported catalyst.

The supports themselves are preferably characterized by a specific surface area of at least about 10 square meters per gram, and more preferably from about 25 to 200 square meters per gram, (as determined by the BET method), and by a pore volume of at least about 0.1 cc./gm, and preferably from about 0.2 to 1.5 cc./gm (as determined by mercury porosimetry).

The catalysts can themselves be formed from a thermally decomposable salt so that a suitable solution of the selected rhenium salt, for example, can then be impregnated on to the surface of a catalyst support followed by calcining at a temperature of at least about 400° C. for sufficient time to activate the catalyst. Generally, a time of from about 1 to 5 hours will be sufficient at a temperature within the range of 300° to 600° C. This calcining step can be performed in air or in the presence of $H_2S$ or an inert gas such as nitrogen, helium and the like. The particular decomposable compound selected will influence the anion associated with the Re and promoter cations in the supported catalyst following the calcining step. Thus, a thio-salt of Re and/or promoter, such as ammonium thiorhenates or ammonium thiomolybdate, will be generally calcined to form a Re sulfide catalyst. Non-thio salts, such as the nitrate, carboxylates, carbonate and the like which do not contain S, will generally yield a Re oxide catalyst on decomposition when the decomposable salt itself contains oxygen or when the calcining is conducted in an $O_2$-containing gas (e.g., air). Similarly, calcining the above S-free Re and promoter salts in the presence of an $H_2S$, COS, or $CS_2$ atmosphere will also provide a catalyst containing Re sulfides.

The selected catalyst components (e.g., rhenium salt such as ammonium perrhenate, the mono- or di-carboxylate of from 1 to 10 carbon atoms, (e.g., the acetate, oxalate and the like), carbonate, nitrate and the like, alone or in combination with a selected promoter compound (e.g., ammonium paramolybdate) are intimately mixed in the presence of a solvent so as to produce a solution or for a flowable paste. Then the selected support is impregnated with this liquid mixture and evaporation is carried out under the selected temperature conditions to obtain a dry solids. Water may be used as the solvent for mixing the catalyst components, but oxygenated organic compounds such as alcohols, ethers, esters, dioxane and the like can also be used.

A particularly preferred catalyst of this invention is prepared by first depositing (e.g., by vacuum impregnation) the selected support (e.g., gamma-alumina) with a thermally decomposable molybdenum compound (e.g., ammonium paramolybdate or thiomolybdate), followed by drying and calcining to form solids having molybdenum salts deposited thereon. Thereafter, the selected decomposable rhenium compound (e.g., ammonium perrhenate) is deposited thereon, e.g., by vacuum impregnation, followed by a second drying and calcining of the solids. If desired, a Group VIII noble metal promoter compound (e.g., a rhodium salt such as rhodium nitrate) can then be deposited on the Mo—Re catalyst, again followed by drying and calcining. Alternatively, the preferred catalyst can be prepared by depositing the selected Group VIII noble metal promoter compound prior to, or simultaneously with, the deposition of the Re compound onto the surface of the solids on which molybdenum has been previously deposited. Each drying step can be performed at temperatures within the range of from about 100° to 300° C. for a time sufficient to remove substantially all water (in the case of use of aqueous solutions of the foregoing Mo, Re and/or Group VIII noble metals salts) or at a temperature above the solvent boiling point to about 300° C., for removal of any other selected solvent used during the impregnation or deposition of the metals, optionally together with passing of an inert gas such as nitrogen over the solids' surface to facilitate the removal of the water or solvent. The calcining temperatures and times are as described above.

Formation of especially preferred supported Mo sulfide solids from thermally decomposable thiomolybdate compounds is more completely described in our copending applications, Ser. Nos. 420,715 and 420,627, filed Sept. 21, 1982, whose disclosures are hereby incorporated by reference.

The supported catalyst thus prepared will generally have a surface area of at least about 5 $m^2$/gm (and preferably at least 40 $m^2$/gm) and can be used in a fixed bed and can also be used in fluidized bed or other conventional means of housing the catalyst particles for ultimate contact with the gaseous reactants.

Oxidation Process

The olefinic hydrocarbons which can be employed as reactants in the process of this invention are those which contain an aliphatic chain of at least two carbon atoms in which there exists at least one aliphatic double bond, —HC=CH—. Suitable olefinic hydrocarbons are those which are normally gaseous as well as those which are liquids at room temperatures but which can exist in the gaseous form at the elevated temperature and pressure conditions which are employed during the reaction. Representative olefinic reactants which can be employed, either alone or in combination, are propylene, 1-butene, 2-butene, 1-pentene, 2-pentene, 1-hexene, 2-hexene, 3-hexene, 3-methyl-1-pentene, cyclobutene, 1-heptene, 2-heptene, 1-octene, 2-octene, 1-nonene, 2-nonene, 1-decene, cyclohexane, cyclooctene, 1-dodecene, 1-hexadecene, allyl benzene, propenyl benzene, 3-phenyl-1-hexene, 4-o-tolyl-1-butene, and 1,6-diphenyl-3-hexene. Thus, suitable olefins include (1) linear mono olefins of 2 to 20 carbon atoms, inclusive of terminal olefins, i.e., olefins, having a terminal $CH_2$=CH— group, and internal olefins having the carbon-carbon double bond, as a —HC=CH— group in an internal carbon-carbon bond of the olefin, and (2) cyclic mono-olefins of 4 to 20 carbon atoms having a —HC=CH— group in the cyclic ring. Particularly suitable for this invention are linear alkenes having from 2 to 10 carbon atoms and cycloalkenes of 4 to 10 carbon atoms, and most preferred are alkenes having from 4 to 10 carbon atoms. Illustrative of these preferred classes of olefin feeds are those comprising 1-butene, 2-butene, 1-hexene, 1-pentene, propene, 1-octene, cyclohexene, cyclopentene, cyclobutene and the like, and mixtures thereof.

Paraffins (such as alkanes of 2 to 20 carbon atoms) and isoolefins (i.e., olefins having a >C=C< group in which one or both carbon atoms are hydrocarbyl substituted, such as 2-methyl-2-butene) can be also present in the gas feed to the oxidation zone in the practice of this invention, but they are essentially unreactive in forming the desired ketones.

Preferred olefinic feeds are olefin gas mixtures obtained from the refining of crude oil. Thus, butene cuts from such refineries typically contain n-butenes (1-butene and 2-butene) which will be converted by this process into 2-butanone, and also typically contain butene and isobutene.

The process of this invention is effected by passing the selected olefin and water vapor over the surface of a catalyst of this invention under conditions such as to maintain a vaporous olefin in the reaction zone. The conditions of temperature and pressure under which this can be performed can vary widely depending on such factors as the particular olefin selected for use, the space velocity of gases through the reactor and other factors. Generally, however, a temperature of from about 125° to 600° C., preferably from about 200° to less than about 400° C., will be entirely suitable. Most preferably, where the alkene comprises butene-1 or butene-2, the temperature within the catalyst reactor is maintained within the range of from about 250° to 375° C. Similarly, for cycloalkenes such as cyclohexene, a temperature in the range of about 125° to about 220° C. is most preferable. The pressures are in no way critical and will generally range from about 0 to 2000 psig, preferably from about 5 to 300 psig, although higher or lower pressures are also suitable.

The space velocity of the total gases through the oxidation reactor are also not critical and can range from 100 to 10,000 v/v/hr., and preferably from about 200 to 6,000 v/v/hr., where "v" represents a unit of volume (e.g., "cc").

The reaction can be carried out either batchwise, continuously, or semi-continuously. In batch operations, the gaseous reactants may be placed, together with the catalyst, in a suitable pressure vessel and allowed to remain there under the desired reaction conditions for a suitable reaction interval, which will generally range from about 0.01 to 10 hours or more, depending on the degree of reaction completeness sought. In continuous operation, the gaseous reactants are passed through a body of the catalyst supported within a reactor vessel, which can be any of the conventional equipment employed by the industry for such reactions.

The oxygen and water vapor can be combined and premixed with, or introduced separately from, the olefin feed, or they can be passed to the reaction vessel via separate conduits. The manner of contacting the water vapor, $O_2$ and olefin is not critical and any of the conventional gas-gas contacting methods employed in the industry may be used.

The ratio of olefin:water vapor can also vary widely. Generally, the molar ratio of olefin:water vapor introduced to the reactor will range from about 2:1 to 1:20, preferably from about 1:1 to 1:10. The molar ratio of olefin:oxygen thus introduced can also vary widely. Generally, the olefin:oxygen molar ratio in the total gases to the reactor will range from about 0.5:1 to 10:1, and more typically from about 1:1 to 5:1. However, ratios outside the foregoing ranges can also be employed.

An inert gaseous diluent such as nitrogen or paraffin can also be introduced together with the other gaseous feeds to the reactor in order to achieve a desired high space velocity and to minimize hot spots which could result in an over-oxidation of the feed and/or reactants during the exothermic ketone formation using the $O_2$-containing feed.

Preferably, the olefin and water vapor are contacted with a non-halide catalyst of this invention and in the substantial absence of free halide (that is a molar ratio of free halide:olefin of less than about $1 \times 10^{-5}:1$) in order to minimize corrosion difficulties.

The ketones which are formed will depend, of course, on the particular olefin(s) employed in the feed. Thus, use of alkene as the olefin will result in forming the corresponding alkanone having the same number of carbon atoms as the alkene fed (acetone from propylene; methyl ethyl ketone from 1-butene, 2-butene or mixtures thereof; cyclohexanone from cyclohexene). The process is particularly suitable for forming alkanones having from 4 to 10 carbon atoms.

The major alcohol product formed in the process of this invention will correspond to the carbon skeleton of the ketone product, e.g., secondary butyl alcohol corresponding to methyl ethyl ketone.

The ketones and alcohols produced by the process of this invention can be recovered from the reaction mixture in any desired manner, such as by distillation or by extraction with water or other solvents followed by distillation. Preferably, at least a portion of the unreacted gases are recovered and recycled to the reactor in addition to fresh feed gases in order to maximize olefin conversion. Alternatively, a series of reactor vessels can be employed and the unreacted gases from the first vessel can then be passed as feed to the second vessel, together with make-up gaseous olefin and water vapor as required.

While not wishing to be limited thereby, it is believed that the ketone product formed by the partial oxidation process of this invention proceeds by way of an alcohol intermediate corresponding to the skeleton structure of the ketone product. It is believed that this is the explanation for the quantity of alcohol product which is also formed and detected in the examples that follow. For example, butene is oxidized to a mixture of ketone and secondary butyl alcohol. Accordingly, our invention also provides a process for contacting such an alcohol with water vapor and $O_2$ in the presence of a catalyst of this invention to form a corresponding ketone. Process parameters including reaction times, space velocities, temperatures, pressures and the like, which are discussed above for the olefin partial oxidation process, are also useful in the embodiment of this invention in which the alcohol is employed as the feed. The molar ratio of alcohol:water vapor is generally from about 0.01:1 to 100:1, and preferably from about 0.1 to 1 to 10:1, and the alcohol:oxygen molar ratio will generally be from about 0.1:1 to 100:1, preferably 1:1 to 10:1. Alcohols which are suitable as feeds correspond to any of the above-discussed product alcohols of this invention. Therefore, particularly suitable are alkanols, and especially secondary alkanols, having from 3 to 10 carbon atoms per molecule. The utility of the catalysts of this invention for conversion of alcohols to ketones can be readily seen from the following examples, and it will also be apparent to one skilled in the art that recycle of recovered alcohol by-product to an olefin-reaction zone using a catalyst of this invention will provide improved overall utilization of an olefin-containing feed as a result of the further reaction of the thus-recycled alcohol by-product.

The gas feed to the process of this invention, employing either olefin or alcohol as the ketone precursor feed-component, will preferably be substantially free of $H_2S$, e.g., will contain less than about 0.01 vol.% $H_2S$ in the gas feed.

The process of this invention can be further illustrated by reference to the following examples wherein percent conversions and selectivities are mole percent.

Product selectivities in the examples were determined by gas chromatographic analysis after steady-state conditions were observed. Products formed were methyl ethyl ketone, CO, $CO_2$, secondary butyl alcohol, butyl mercaptan and the balance unknowns. In the Examples, the gaseous effluents from the reactor were analyzed for butene consumed, using isobutane as a standard and employing response factors determined for the GC by calibration with a known gas mixture.

EXAMPLE 1

Gamma-alumina (15 cc.; 12–20 mesh; 100 m$^2$/gm surface area; 0.45 cc./gm pore volume; Alfa Products) was dried in air in a Linberg furnace at 500° C. for 3 hours to give a dry weight of 12.89 grams. Ammonium perrhenate [NH$_4$ReO$_4$] (1.30 grams) was dissolved in distilled water to form a 5.5 cc. aqueous solution and transferred into a 60 cc. dropping funnel. The catalyst support was placed in a 125 cc. glass filtering flask equipped with a side arm for pulling a vacuum, and the filtering flask was attached to a dropping funnel using a rubber stopper. After evacuation to a pressure of −15 in Hg, the ammonium perrhenate solution was added dropwise to the catalyst support to achieve complete wetness. The impregnated wet catalyst was placed in a stainless steel gauze boat and dried in air at 125° C. for 1.25 hour, 250° C. for 0.75 hour and 350° C. for 1 hour, and finally calcined in air by raising the furnace temperature to 500° C. (at a rate of about 10° C./min.), which was maintained for 3 hours. After the drying and calcining procedure, the resulting catalyst was found to comprise rhenium oxide on gamma-alumina and to contain 7.1 wt.% Re, calculated as the metal, based on the weight of the catalyst support.

Ten cc. of the foregoing oxide catalyst and 20 cc. of fused ceramic inerts (12–20 mesh) were well mixed and loaded into a test reactor which comprised a 24-inch (0.38 inch ID) stainless steel tubular reactor equipped with gas inlets and gas outlets at opposing ends of the tubular reactor. The reactor was then heated to a temperature of 303° C. (which was maintained by means of electric heating tape and a Gardsman temperature control). Temperatures in the reactor were determined by means of a thermocouple positioned in the center of the catalyst bed. A gaseous mixture containing butene-1, oxygen, nitrogen and water vapor was passed to the reactor, the oxygen and nitrogen being employed as a 10:90 vol:vol mixture of oxygen and nitrogen. The feed rates for these gaseous components and the reaction temperature were 60 cc. per minute of butene, 730 cc. per minute of the oxygen:nitrogen mixture, and 224 cc. per minute of water vapor. The total gas hourly space velocity of the gaseous mixture through this reactor was 6084 cc/cc/hr. A gaseous inlet pressure of 7.1 psig was employed throughout the reaction (0.4 hrs.). A gaseous effluent was continuously withdrawn from the reactor and was sampled and analyzed by means of an on-line gas chromatograph. After achieving steady conditions, methyl ethyl ketone was found to have been formed in a selectivity of about 86.6% at a butene conversion of 5.6%. Selectivity to carbon dioxide was 3.6% and no carbon monoxide was found.

EXAMPLE 2

In a separate run, the catalyst used in Example 1 was contacted with a butene feed under the same conditions except that the gaseous feed to the reactor (298° C.) was 102 cc. per minute of butene-1, 730 cc. per minute of the oxygen:nitrogen mixture, and 224 cc. per minute of water vapor, providing a gas hourly space velocity of 6336 cc/cc/hr. Methyl ethyl ketone was found to have been formed in a selectivity of 87.4%, as determined by sampling after 3.0 hours of reaction. (Butene conversion in this run was not determined.) No selectivity loss to carbon dioxide and carbon monoxide was detected.

EXAMPLE 3

The rhenium oxide catalyst employed in Example 2 above (still mixed with the inerts) was sulfided in the reactor by contacting the oxide catalyst with a gas mixture of hydrogen sulfide (190 cc./min.; charged as 6 vol.% H$_2$S in N$_2$) and H$_2$ (230 cc./min.) at a temperature of 325° C. and a gas inlet pressure of 9 psig, for 3 hours. The resulting solids were then contacted under the same flow conditions with H$_2$ (520 cc./min) to strip out any absorbed, unreacted H$_2$S. The catalyst was then determined to comprise rhenium sulfide, and to contain rhenium in an amount of about 7.1 wt.%, calculated as the element, based on the total weight of the catalyst support.

The rhenium sulfide catalyst was then contacted with a butene feed of the following composition employed the procedure of Example 1 employing a gas inlet pressure of about 8.5 psig and reaction temperature of 298° C.: 60 cc. per minute of butene, 380 cc. per minute of the oxygen:nitrogen mixture and 224 cc. per minute of water vapor. The total gas hourly space velocity during the run (2.0 hrs.) was 3984 cc/cc/hr. At a 4.8% conversion methyl ethyl ketone was found to be formed in a selectivity of 83.3%. Carbon dioxide selectivity was 3.6% and secondary butyl alcohol selectivity was 2.9%. No selectivity loss to carbon monoxide was observed.

EXAMPLE 4

The rhenium sulfide catalyst of Example 3 was employed in a second such run at a reaction temperature of 294° C. and a gas inlet pressure of 8.5 psig for 4.5 hours. In this Example, the gaseous feed to the reactor comprised 60 cc. per minute of butene, 730 cc. per minute of the oxygen:nitrogen mixture and 224 cc. per minute of water vapor. The total gas hourly space velocity was therefore 6084 cc/cc/hr. At a 3.4% butene conversion, methyl ethyl ketone selectivity was 88.4%. No selectivity loss to carbon dioxide or carbon monoxide was observed. Secondary butyl alcohol selectivity was observed to be 1.8%.

EXAMPLE 5

Gamma-alumina (25 cc.; 12–20 mesh; Alfa Products) was dried in a Lynberg furnace at 500° C. for 3 hours in air to give a dry weight of 21.0 grams. Ammonia perrhenate (1.52 grams) was dissolved in distilled water to provide 24 cc. of an aqueous solution. Following the procedure of Example 1, the support was vacuum impregnated three times, each impregnation employing 8.0 cc. of the above aqueous ammonium perrhenate solution. After each impregnation, the impregnated solids were dried in nitrogen for one-half hour at 125° C., followed by one-half hour at 250° C. and then calcined in air at 500° C. for 3 hours. After the third impregnation, the solids were allowed to cool to room temperature and the material was divided into two equal parts. The first one half of the impregnated solids was then impregnated twice with an aqueous solution of rhodium trinitrate using the drying and calcining procedure described in Example 1. The rhodium trinitrate solution comprised, in each impregnation 4.0 cc. of an aqueous solution containing 0.521 gram of rhodium trinitrate. After each impregnation with the rhodium salt, the solids were dried and calcined as described above. The mixed rhenium oxide:rhodium oxide on alumina catalyst was then mixed with inerts and sulfided with hydrogen sulfide gas using the procedure described above in Example 3. The catalyst thereby obtained was found to comprise 1.5 wt.% rhodium and 5.0 wt.% rhenium, calculated as the metals, based on the weight of the catalyst support.

Following the procedure of Example 1, a series of 5 runs were conducted using a reaction temperature of 300° C., and a gas inlet pressure of about 7 psig, with varying compositions of gaseous feed to the reactor. Water vapor feed in each run was 224 cc. per minute. The data thereby obtained are set forth in Table I below.

Run 3 shows that $H_2S$ is not a desired component of the feed to the process using a Rh—Re sulfide catalyst.

drying of the solids under nitrogen in the furnace at 125° C. for 1 hour, 200° C. for 1 hour, and 350° C. for 1 hour. The dried solids were then calcined in the furnace by raising the furnace temperature to 500° C. (at a rate of 10° C. per minute) which was then maintained for 3 hours, under $N_2$. This rhodium sulfide catalyst mixed with inerts and employed in Runs C to E, to be described below.

The selected rhodium sulfide catalyst prepared as above were then employed in separate runs for butene oxidation using the procedure described above for Example 3, employing the conditions of reaction set forth in Table II below. The reaction temperature in Run A was 303° C. and in Runs B to E was 300° C. The gas

TABLE I

| | | | | | Rh—Re Sulfide Catalyst | | | | | | |
|---|---|---|---|---|---|---|---|---|---|---|---|
| Run | Time | Butene Feed | $O_2/N_2$[1] Feed | $H_2S$ Feed | GHSV[2] | Butene | | | % Selectivity | | |
| No. | (hrs.) | (cc/min) | (cc/min) | (cc/min) | cc/cc/hr | Conv. (%) | MEK[3] | $CO_2$ | CO | SBA[4] | $C_4SH$[5] |
| 1 | 1.0 | 31 | 380 | 0 | 3138 | 43.6 | 50.7 | 18.9 | 5.6 | ND | 9.8 |
| 2 | 2.0 | 60 | 730 | 0 | 6084 | 14.6 | 51.9 | 23.0 | 6.1 | ND | 3.1 |
| 3 | 2.5 | 60 | 730 | 65 | 6474 | 39.5 | 6.0 | 13.9 | 10.8 | ND | 58.8 |

[1]Fed as 10 vol. % $O_2$ in $N_2$.
[2]Total gas hourly space velocity
[3]Methyl ethyl ketone.
[4]Secondary butyl alcohol.
[5]Butyl mercaptan.

EXAMPLE 6

Employing the catalyst preparation procedure of Example 1, a rhodium oxide on gamma-alumina catalyst was prepared by vacuum impregnation of the gamma-alumina support with a 9.0 ml. aqueous solution containing 1.0 grams of rhodium trinitrate, followed by drying in nitrogen at 150° C. for 1 hour, 250° C. for 1 hour, and 350° C. for 2 hours, and by calcining in air at 500° C. for 3 hours. The rhodium oxide catalyst was then mixed with inerts and subjected to the $H_2S$ sulfiding/$H_2$ stripping procedure of Example 3. The rhodium sulfide on gamma-alumina catalyst thereby obtained was found to contain 1.5 wt.% rhodium, calculated as the metal, based on the weight of the catalyst support. This catalyst was employed in Runs A and B, to be described in more detail below.

A second rhodium on gamma-alumina catalyst containing 1.0 wt.% rhodium (calculated as the metal) was prepared from $RhCl_3 \cdot 3H_2O$ and ammonium sulfide by vacuum impregnation of an aqueous rhodium chloride solution (8 cc.; containing 0.565 grams of the hydrated rhodium trichloride), following the procedure of Example 1. The impregnated solids were dried in the oven at 125° C. for 3 hours under nitrogen and 25 cc. of the resulting solids was then reacted with an aqueous solution containing 0.70 gram of ammonium sulfide [$(NH_4)_2S$] by contacting for 30 minutes at 25° C. in a glass flask. The resulting solids were then washed with distilled water (3 equal portions of 10 cc.) to remove any excess unreacted ammonium sulfide, followed by inlet pressure in each run was about 7 psig, and the water vapor injection rate in Run D was 112 cc. per minute and in all other runs was 224 cc. per minute.

The data thereby obtained are set forth in Table II below.

Under comparable conditions, the rhenium-rhodium sulfide catalysts of Example 1 obtained significantly improved conversions to ketone product while providing decreased selectivity loss to carbon dioxide and carbon monoxide by-products. Comparing Run 6-C and Run 5-2, each conducted under similar space velocities and at 300° C., it can be seen that the rhodium-rhenium sulfide catalyst of this invention provided over a 35 percentage point advantage in methyl ethyl ketone selectivity (51.9% in Example 5-2 versus 16.5% in Comparative Example 6-C) while at the same time providing almost a 46 percentage point advantage in decreased total selectivity to carbon dioxide and carbon monoxide (29.1% $CO_2+CO$ in Example 5-2 versus 75.0% in Comparative Example 6-C). Similarly, the rhodium-rhenium sulfide catalyst of Example 5-1 provided and 18 percentage point increase in methyl ethyl ketone selectivity (50.7% versus 32.7%) and over 64 percentage points decrease in total selectivity loss to carbon dioxide and carbon monoxide ($CO_2+CO$: 24.5 in Example 5-1 versus 88.9% in Comparative Example 6-D), as compared to the rhodium sulfide catalyst of Comparative Example 6, Run D, which runs were conducted under similar conditions of temperature and gas hourly space velocities.

TABLE II

| | | | | | Comparison: Rh Sulfide Catalyst | | | | | | |
|---|---|---|---|---|---|---|---|---|---|---|---|
| Run | Time | Butene Feed | $O_2/N_2$[1] Feed | $H_2S$ Feed | GHSV[2] | Butene | | | % Selectivity | | |
| No. | (hrs.) | (cc/min) | (cc/min) | (cc/min) | cc/cc/hr | Conv. (%) | MEK[3] | $CO_2$ | CO | SBA[4] | $C_4SH$[5] |
| A | 0.5 | 60 | 730 | 0 | 6084 | 18.0 | 51.9 | 36.0 | 2.8 | 0.3 | 1.6 |
| B | 1.5 | 60 | 730 | 65 | 6474 | 29.0 | 8.9 | 16.0 | 13.1 | 0.3 | 46.1 |
| C | 0.5 | 60 | 730 | 0 | 6084 | 14.3 | 16.5 | 63.6 | 11.4 | — | 0.2 |
| D | 1.5 | 31 | 380 | 0 | 3138 | 12.9 | 32.7 | 56.2 | 2.4 | — | 0.7 |

TABLE II-continued

| | | | | Comparison: Rh Sulfide Catalyst | | | | | | |
|---|---|---|---|---|---|---|---|---|---|---|
| Run No. | Time (hrs.) | Butene Feed (cc/min) | $O_2/N_2$[1] Feed (cc/min) | $H_2S$ Feed (cc/min) | GHSV[2] cc/cc/hr | Butene Conv. (%) | % Selectivity | | | |
| | | | | | | | MEK[3] | $CO_2$ | CO | SBA[4] | $C_4SH$[5] |
| E | 2.0 | 60 | 730 | 65 | 6474 | 43.4 | 7.6 | 21.9 | 25.0 | — | 31.6 |

[1] Fed as 10 vol. % in $O_2$ in $N_2$.
[2] Total gas hourly space velocity
[3] Methyl ethyl ketone.
[4] Secondary butyl alcohol.
[5] Butyl mercaptan.

EXAMPLE 7

A 10.2 gram portion of the supported rhenium oxide catalyst prepared as in Example 5 was impregnated with 8 cc. of an aqueous solution containing 0.414 gram of palladium nitrate [$Pd(NO_3)_2 \cdot H_2O$], using the double impregnation, drying and calcining steps described above for Example 5. The mixed Re-Pd oxide catalyst was then mixed with inerts and sulfided using the procedure of Example 3. The mixed palladium sulfide:rhenium sulfide on gamma-alumina catalyst was found to contain 1.5 wt.% palladium and 5.0 wt.% rhenium, calculated as the metals, based on the weight of the catalyst support. This oxide catalyst was then mixed with inerts and employed in a series of runs using the procedure of Example 1. Runs 1 and 3 employed a reaction temperature of 300° C. Run 2 employed a reaction temperature of 250° C. In each case, the gas inlet pressure was about 7 psig and the water vapor feed rate was 224 cc./min. The data thereby obtained are set forth in Table III below.

nium perrhenate ($NH_4ReO_4$) followed by drying and calcining in air at the temperatures and for the times described in Example 1. The Re-Mo oxide catalyst thereby obtained was found to contain 3.7 wt.% rhenium and 9.5 wt.% molybdenum, calculated as the metals, based on catalyst support. Ten cc. of this catalyst was then employed (with inerts, per Example 1) in Runs 1 and 2 for butene oxidation.

A separate rhenium-molybdenum catalyst was prepared by vacuum impregnating 8.9 grams of gamma-alumina with 22 cc. of an aqueous solution of ammonium thiomolybdate (containing 1.73 grams of $(NH_4)_2MoS_4$) using the procedure of Example 1, followed by drying of the impregnated solids in helium at 125° C. for one hour, 250° C. for one hour, and 350° C. for 3 hours. This catalyst impregnation procedure was then repeated six times, and the resulting molybdenum sulfide catalyst was vacuum impregnated with Re using the procedure of Example 1 and employing 3.7 cc. of an aqueous solution containing 0.391 gram of ammonium perrhenate, followed by drying in air at 125° C. for 1

TABLE III

| | | | | Pd—Re Sulfide Catalyst | | | | | | |
|---|---|---|---|---|---|---|---|---|---|---|
| Run No. | Time (hrs.) | Butene Feed (cc/min) | $O_2/N_2$[1] Feed (cc/min) | $H_2S$ Feed (cc/min) | GHSV[2] cc/cc/hr | Butene Conv. (%) | % Selectivity | | | |
| | | | | | | | MEK[3] | $CO_2$ | CO | SBA[4] | $C_4SH$[5] |
| 1 | 2.0 | 60 | 730 | 65 | 6474 | 14.3 | 39.5 | 4.5 | 2.2 | 10.0 | 35.6 |
| 2 | 3.0 | 60 | 730 | 65 | 6474 | 2.4 | 40.7 | 0 | 0 | 26.5 | 16.7 |
| 3 | 4.0 | 60 | 730 | 0 | 6084 | 7.4 | 17.8 | 36.4 | 22.7 | 5.9 | 3.0 |

[1] Fed as 10 vol. % in $O_2$ in $N_2$.
[2] Total gas hourly space velocity
[3] Methyl ethyl ketone.
[4] Secondary butyl alcohol.
[5] Butyl mercaptan.

EXAMPLE 8

Employing the procedure of Example 1, gamma-alumina (12.9 grams) was impregnated with ammonium heptamolybdate by use of an aqueous solution containing 2.19 grams of the ammonium paramolybdate salt, followed by drying and calcining in nitrogen at the temperature conditions described above for Example 1. Thereafter, the solids were impregnated with ammohour, 250° C. for 1 hour and 350° C. for 1 hour and calcining in air at 500° C. for 3 hours. The resulting rhenium-molybdenum catalyst was found to comprise 2.8 wt.% rhenium and 7.5 wt.% molybdenum, calculated as the respective metals, based on the weight of the catalyst support. Ten cc. of the catalyst was then mixed with inerts, sulfided as in Example 3 and employed in Runs 3 and 4, using the procedure of Example 1. Data are summarized in Table IV.

TABLE IV

| | | | | Re—Mo Oxide Catalysts | | | | | | | | |
|---|---|---|---|---|---|---|---|---|---|---|---|---|
| | | | | Gas Feed (cc/min.) | | | GHSV[2] | | | | | |
| Run No. | Temp. (°C.) | Time (hrs) | Press. psig | Butene | $O_2:N_2$[1] | $H_2O$ Vapor | (cc/cc/ hr) | Butene Conv. (%) | % Selectivities | | | |
| | | | | | | | | | MEK | $CO_2$ | CO | SBA[4] | $C_4SH$[5] |
| 1 | 308 | 0.5 | 7 | 60 | 380 | 224 | 3984 | — | 78.5 | 0 | 0 | 6.1 | 0 |
| 2 | 296 | 1.5 | 7 | 102 | 730 | 224 | 6338 | 3.4 | 77.7 | 0 | 0 | 10.5 | 0 |
| 3 | 302 | 7.5 | 9 | 60 | 730 | 224 | 6084 | 8.8 | 81.4 | 0 | 2.6 | 0 | 0 |

TABLE IV-continued

Re—Mo Oxide Catalysts

| Run No. | Temp. (°C.) | Time (hrs) | Press. psig | Gas Feed (cc/min.) Butene | $O_2:N_2$[1] | $H_2O$ Vapor | GHSV[2] (cc/cc/hr) | Butene Conv. (%) | % Selectivities MEK[3] | $CO_2$ | CO | SBA[4] | $C_4SH$[5] |
|---|---|---|---|---|---|---|---|---|---|---|---|---|---|
| 4 | 300 | 1.8 | 9 | 60 | 380 | 224 | 3984 | 7.6 | 84.4 | 0 | 2.1 | 0 | 0 |

[1] Fed as 10 vol. % $O_2$ in $N_2$.
[2] Total gas hourly space velocity.
[3] Methyl ethyl ketone.
[4] Secondary butyl alcohol.
[5] Butyl mercaptan.

EXAMPLE 9

A rhenium-molybdenum sulfide catalyst was prepared using three different methods. Each sulfided catalyst, supported on gamma-alumina, was then employed in a series of runs for butene oxidation.

The first sulfide catalyst was prepared by subjecting the rhenium-molybdenum oxide catalyst which was employed in Runs 1 and 2 of Example 8 to the in situ $H_2S$ sulfiding/$H_2$ stripping procedure of Example 3. The resulting sulfided catalyst was found to comprise 2.8 wt.% rhenium and 7.5 wt.% molybdenum, calculated as the metals. This sulfided catalyst was then mixed with inerts and employed in Run 1 of Table V as in Example 1.

The second Re-Mo sulfide catalyst was prepared employing the procedure of Example 1 by vacuum impregnating the gamma-alumina support (8.9 grams) with one-sixth of 22 cc. aqueous solution containing 2.284 grams of ammonium tetrathiomolybdate, followed by drying in air at 125° C. for 1 hour and 250° C. for 1 hour, and at 350° C. for 3 hours. This molybdenum impregnation step was then repeated five times, followed each time by the three-step drying process, and the resulting solids were then vacuum impregnated with 3.7 cc. of an aqueous solution containing 0.391 grams of ammonium perrhenate again employing the identical drying procedure. Finally, after again drying in the three-stage procedure, the solids were calcined in air at a temperature of 500° C. for 3 hours and then mixed with inerts and sulfided using the $H_2S$ sulfiding/$H_2$ stripping procedure of Example 3. The resulting sulfided catalyst was employed in Run 2 of Table V below.

The third Re—Mo sulfide catalyst was prepared by refluxing the selected amount of gamma-alumina (12.6 grams) in 50 cc. of methanol containing 2.26 grams of ammonium paramolybdate and 0.68 gram of ammonium perrhenate for 1.5 hours followed by removing most of the methanol by heating (65° C., 1 hour) while passing $N_2$ through the solid/liquid mixture and drying in air at 125° C. for 1 hour, 250° C. for 1 hour, 350° C. for 1 hour to remove the methanol and calcining in air at 500° C. for 3 hours to obtain the corresponding mixed oxide of rhenium and molybdenum on the gamma-alumina. The oxide catalyst was thereafter mixed with inerts and treated using the $H_2S$ sulfiding/$H_2$ stripping procedure of Example 3 to obtain a rhenium-molybdenum sulfide catalyst supported on gamma-alumina containing about 3.7 wt.% and 7.5 wt.% rhenium and molybdenum, respectively, calculated as the elements. This sulfide catalyst was then employed in Runs 3, 4 and 5 in Table V below using the method of Example 1.

TABLE V

Re—Mo Sulfide Catalysts

| Run No. | Temp. (°C.) | Time (hrs) | Press. psig | Gas Feed (cc/min.) Butene | $O_2:N_2$[1] | $H_2O$ Vapor | GHSV[2] (cc/cc/hr) | Butene Conv. (%) | % Selectivities MEK[3] | $CO_2$ | CO | SBA[4] | $C_4SH$[5] |
|---|---|---|---|---|---|---|---|---|---|---|---|---|---|
| 1 | 300 | 7.7 | 7 | 60 | 380 | 224 | 3984 | 28.3 | 70.3 | 7.6 | 2.5 | 4.1 | 0 |
| 2 | 310 | 3.4 | 9.7 | 102 | 730 | 224 | 6336 | 6.6 | 86.4 | 0 | 1.3 | 12.0 | 0 |
| 3 | 302 | 0.9 | 8.9 | 102 | 730 | 224 | 6336 | 14.0 | 68.2 | 7.0 | 4.7 | 6.3 | 6.0 |
| 4 | 291 | 7.3 | 9.1 | 60 | 730 | 224 | 6084 | 14.3 | 74.7 | 2.0 | 2.0 | 11.3 | 0 |
| 5 | 298 | 16.2 | 9.3 | 60 | 380 | 224 | 3984 | 9.3 | 76.7 | 2.2 | 1.1 | 10.8 | 0 |

[1] Fed as 10 vol. % $O_2$ in $N_2$.
[2] Total gas hourly space velocity.
[3] Methyl ethyl ketone.
[4] Secondary butyl alcohol.
[5] Butyl mercaptan.

EXAMPLE 10 FOR COMPARISON

Employing the procedure of Example 8 above, 37.1 grams of gamma-alumina were vacuum impregnated with ammonium heptamolybdate, followed by drying in $N_2$ at 125° C. for 1 hour, 250° C. for 1 hour, and 350° C. for 1 hour and calcining in $N_2$ at 500° C. for 3 hours.

The resulting molybdenum-oxide catalyst, supported on gamma-alumina, was found to contain 9.5 wt.% molybdenum, calculated as the metal. This oxide catalyst was then mixed with inerts and employed in Runs A and B of Table VI below using the procedure of Example 1.

The catalyst employed in Runs C and D of Table VI comprised the corresponding sulfided catalyst which was prepared by the in situ sulfiding/stripping procedure of Example 3.

The data thereby obtained are set forth in Table VI below.

In comparing the molybdenum oxide catalysts of Comparative Example 10, Runs A and B, with the Re—Mo oxide catalysts of this invention used in Example 8, it can be seen that the rhenium-catalyst of this invention permitted the formation of the methyl ethyl ketone product in high selectivities with only minimal, if any, selectivity loss to an oxide of carbon. Thus, the rhenium-molybdenum oxide catalyst in Example 8-3 provided 81.4% methyl ethyl ketone selectivity at 8.8% butene conversion and formed only 2.6% selectivity loss to carbon monoxide with no carbon dioxide being detected. In contrast, Comparative Example 10-A suffered almost 10% in selectivity loss to total carbon dioxide and carbon monoxide under similar gas flow conditions.

Similarly, the molybdenum sulfide catalysts of Comparative Example 10, Runs C and D, formed only up to about 69% selectivity methyl ethyl ketone with up to about 12% selectivity loss to carbon dioxide and carbon monoxide. In contrast, the rhenium-molybdenum sulfide catalyst of Example 9 formed as much as 86.4% selectivity to methyl ethyl ketone with as little as 1.3% selectivity loss to carbon dioxide and carbon monoxide an aqueous solution containing 0.57 gram of ammonium perrhenate, in a single vacuum impregnation, followed by drying in nitrogen and calcining in air according to the drying and calcining procedure used in Example 5. This single-step vacuum impregnation, drying and calcining procedure was then repeated, using 5 cc. of an aqueous solution containing 0.39 grams of rhodium trinitrate in the vacuum impregnations.

The oxide catalyst thereby obtained was found to contain 1.0 wt.% rhodium, 3.1 wt.% rhenium and 7.8 wt.% tungsten, calculated as the respective element. The oxide catalyst thereby obtained was mixed with inerts employed in Runs 1 and 2 of Table VII below.

After Run 2, the oxide catalyst was sulfided using the in situ sulfiding/stripping procedure of Example 3, and was employed in Run 3.

TABLE VII

Rh—Re—W Catalysts

| Run No. | Temp. (°C.) | Time (hrs) | Press. psig | Gas Feed (cc/min.) Butene | $O_2:N_2$[1] | $H_2O$ Vapor | $GHSV$[2] (cc/cc/hr) | Butene Conv. (%) | % Selectivities MEK | $CO_2$ | CO | SBA[4] | $C_4SH$[5] |
|---|---|---|---|---|---|---|---|---|---|---|---|---|---|
| | | | | | | Rh—Re—W Oxide | | | | | | | |
| 1 | 303 | 0.7 | 7 | 60 | 380 | 224 | 3984 | 30.6 | 74.0 | 10.9 | 0.3 | 5.2 | 0 |
| 2 | 305 | 3.2 | 7 | 60 | 730 | 224 | 6084 | 31.8 | 50.3 | 0.7 | 10.3 | 4.1 | 0 |
| | | | | | | Rh—Re—W Sulfide | | | | | | | |
| 3 | 294 | 6.0 | 7 | 66 | 380 | 224 | 4020 | 27.5 | 72.0 | 9.9 | 1.2 | 4.5 | 0 |

[1] Fed as 10 vol. % $O_2$ in $N_2$.
[2] Total gas hourly space velocity.
[3] Methyl ethyl ketone.
[4] Secondary butyl alcohol.
[5] Butyl mercaptan.

(Run 2 of Example 9).

TABLE VI

Comparison: Mo Catalysts

| Run No. | Temp. (°C.) | Time (hrs) | Press. psig | Gas Feed (cc/min.) Butene | $O_2:N_2$[1] | $H_2O$ Vapor | $GHSV$[2] (cc/cc/hr) | Butene Conv. (%) | % Selectivities MEK | $CO_2$ | CO | SBA[4] | $C_4SH$[5] |
|---|---|---|---|---|---|---|---|---|---|---|---|---|---|
| | | | | | | Mo—Oxide | | | | | | | |
| A | 300 | 2.0 | 7 | 60 | 730 | 224 | 6084 | 9.1 | 80.6 | 6.9 | 2.8 | 8.1 | 0 |
| B | 305 | 5.0 | 7 | 102 | 730 | 224 | 6338 | 20.4 | 71.0 | 3.8 | 1.9 | 4.2 | 0 |
| | | | | | | Mo—Sulfide | | | | | | | |
| C | 305 | 5.2 | 7 | 60 | 730 | 224 | 6084 | 15.1 | 62.6 | 10.0 | 2.0 | 13.6 | 0.9 |
| D | 298 | 6.0 | 7 | 102 | 730 | 224 | 6338 | 12.6 | 68.8 | 5.8 | 1.9 | 9.6 | 0.9 |

[1] Fed as 10 vol. % $O_2$ in $N_2$.
[2] Total gas hourly space velocity.
[3] Methyl ethyl ketone.
[4] Secondary butyl alcohol.
[5] Butyl mercaptan.

EXAMPLE 11

A trimetallic oxide catalyst comprising a mixture of oxides of rhodium, rhenium and tungsten, supported on gamma-alumina was prepared by vacuum impregnation of the dried gamma-alumina (38.8 grams) with ammonium tungstate [$(NH_4)_{10}W_{12}O_{41}$], followed by a stepwise impregnation with ammonium perrhenate after which rhodium trinitrate was impregnated.

The support was impregnated with the tungsten compound using 16 cc. of an aqueous solution containing 0.72 grams of ammonium tungstate, followed by drying at 250° C. in nitrogen. This impregnation and drying procedure was repeated 5 additional times. Then, the final dried solids were heated at 350° C. for 2 hours in air and then calcined in air at 500° C. for 3 hours to convert the metal salt to the oxide form. One third of these solids was then vacuum impregnated with 5 cc. of

EXAMPLE 12 FOR COMPARISON

Employing the procedure described above for Example 11, a rhodium-tungsten oxide catalyst, supported on gamma-alumina was prepared by six separate vacuum impregnations of 38.8 grams of gamma-alumina with the ammonium tungstate salt, followed in each impregnation by a drying and calcining in each step. Thereafter, rhodium trinitrate was vacuum impregnated, again followed by drying and calcining in air to form the desired oxide catalyst. This oxide catalyst was found to comprise 1.0 wt.% rhodium and 7.8 wt.% tungsten, calculated as the elements. The data thereby obtained in a butene-1 oxidation using this catalyst (mixed with inerts) as in Example 1, at two different temperature conditions, are set forth below in Runs A and B of Table VIII.

After Run B, the oxide catalyst was sulfided using the in situ sulfiding/stripping procedure of Example 3. The rhodium-tungsten sulfided catalyst, supported on gamma-alumina, was then employed using the procedure of Example 1 in a butene-1 oxidation. The data thereby obtained are set forth as Runs C and D in Table VIII below.

The above gamma-alumina impregnation procedure was repeated with ammonium tungstate except that no rhodium trinitrate was impregnated. Thus, the gamma-alumina (38.8 grams) was subjected to six separate vacuum impregnations with the aqueous solution of ammonium tungstate, followed by the drying and calcining after each impregnation using the above-described procedure. The resulting tungsten oxide catalyst was found to comprise 7.8 wt.% tungsten, calculated as the element, based on the weight of the total catalyst support. This tungsten catalyst was then employed, after mixing with inerts, per the procedure of Example 1 in a butene-1 oxidation, as indicated in Runs E and F in Table VIII below. (Ten cc. of the oxide catalyst was used.)

At the end of Run F, the tungsten oxide catalyst was subjected to the in situ sulfiding/stripping procedure of Example 3 to form a tunsten sulfide catalyst, which was then used in a separate Run G as indicated in Table VIII below.

Comparing the trimetallic rhenium-rhodium-tungsten oxide catalysts of Example 11 with the rhodium-tungsten and tungsten oxide catalysts of Comparative Example 12, it can be seen that the rhenium-catalyst of this invention illustrated in Example 11 provide high selectivity to ketone and alcohol product with minimal selectivity loss to the carbon dioxide and carbon monoxide by-products which are undesirable. For example, the rhenium-containing catalyst of Example 1, Run 1, formed the ketone product in a selectivity of 74.0% with only 11.2% total selectivity loss to carbon dioxide and carbon monoxide, as contrasted with Comparative Example 12-A which used similar gas flow rates and which obtained the ketone selectivity of only 56.3% and suffered a total selectivity loss of 17.0% to carbon dioxide and carbon monoxide using a rhodium-tungsten oxide catalyst in the absence of rhenium. In further contrast, the tungsten oxide catalyst of Comparative Example 12-E produced only 68.9% selectivity to ketone and suffered a 20.4% selectivity loss to the carbon dioxide and carbon monoxide by-products.

Similarly, the rhenium-rhodium-tungsten sulfide catalyst of Example 11, Run 3, formed a ketone in a selectivity (72.0%) which was significantly higher than was observed with rhodium-tungsten sulfide catalyst (56.4% and 43.1% in Run C and D, respectively) and tungsten sulfide catalyst (28.1% in Run G). Comparable benefits and decreased selectivity loss, carbon dioxide and carbon monoxide with the trimetallic rhenium-containing sulfide catalyst of Example 3 are also seen in this comparison.

TABLE VIII

Comparison: Rh—W and W Catalysts

| Run No. | Temp. (°C.) | Time (hrs) | Press. psig | Gas Feed (cc/min.) Butene | $O_2:N_2$[1] | $H_2O$ Vapor | GHSV[2] (cc/cc/hr) | Butene Conv. (%) | % Selectivities MEK[3] | $CO_2$ | CO | SBA[4] | $C_4SH$[5] |
|---|---|---|---|---|---|---|---|---|---|---|---|---|---|
| Rh—W Oxide |
| A | 308 | 7.5 | 7 | 60 | 380 | 224 | 3984 | 32.4 | 56.3 | 14.7 | 2.3 | 12.6 | 0 |
| B | 312 | 9.9 | 7 | 102 | 730 | 224 | 6338 | 19.2 | 46.9 | 22.7 | 5.6 | 7.0 | 0 |
| Rh—W Sulfide |
| C | 316 | 0.5 | 7 | 60 | 380 | 224 | 3984 | 14.8 | 56.4 | 22.5 | 0 | 9.5 | 0 |
| D | 310 | 3.8 | 7 | 102 | 730 | 224 | 6338 | 27.5 | 43.1 | 13.5 | 2.6 | 12.8 | 2.6 |
| W Oxide |
| E | 301 | 3.0 | 7 | 60 | 380 | 224 | 3984 | 14.3 | 68.9 | 18.8 | 1.6 | 0 | 0 |
| F | 293 | 3.6 | 7 | 102 | 730 | 224 | 6338 | 9.8 | 67.7 | 14.4 | 1.3 | 0 | 0 |
| W Sulfide |
| G | 310 | 1.0 | 7 | 60 | 730 | 224 | 6084 | 28.0 | 28.1 | 21.4 | 8.6 | 0 | 0 |

[1]Fed as 10 vol. % $O_2$ in $N_2$.
[2]Total gas hourly space velocity.
[3]Methyl ethyl ketone.
[4]Secondary butyl alcohol.
[5]Butyl mercaptan.

EXAMPLE 13

Thirty cc. of gamma-alumina (12–20 mesh) was heated in air at 500° C. for 3 hours using the procedure of Example 1 to provide a dry weight of 26.4 grams. Following the exact impregnation procedure of Example 1, 10.6 cc. of an aqueous solution containing 4.63 grams of ammonium paramolybdate in distilled water was impregnated onto the solids, after which the wet catalyst was dried in air at 125° C. for 1 hour, 250° C. for 1 hour, and 350° C. for 1 hour, followed by calcining in air at 500° C. for 3 hours. Upon cooling, the solids were then impregnated with 10.3 cc. of an aqueous solution containing 1.41 grams of ammonium perrhenate, after which the same four-step drying and calcining procedure was used. Finally, these solids were impregnated with a 10.3 cc. aqueous solution containing 0.57 grams employed in nitrate, again followed by the same four-step drying and calcining procedure. The thus-produced solids were found to comprise mixed oxides of palladium, rhenium and molybdenum and to contain 1.08 wt.% Pd, 3.7 wt.% Re, and 9.5 wt.% Mo, calculated as the respective elements, on the basis of the weight of the catalyst support.

Ten cc. of this catalyst was then well mixed with 10–20 mesh fused ceramic inerts, and sulfided using the procedure of Example 3 and then employed in an olefin oxidation following the procedure of Example 1, using the same gas feed composition and feed rates of Run 1 of Example 11, at a reaction temperature of 310° C. and a gas inlet pressure of 9.7 psig. At a butene conversion of 6.5%, the following selectivities were observed: 58.3% methyl ethyl ketone; 5.3% secondary butyl alcohol; 11.3% $CO_2$; 5.0% CO; and 14.0% secondary butyl mercaptan.

EXAMPLE 14

TABLE IX

| Run No. | Time. (hrs) | Temp (°C.) | Press. psig | Gas Feed (cc/min.) | | H$_2$O Vapor | GHSV[3] (cc/cc/ hr) | Butene Conv. (%) | % Selectivities | | | | |
|---|---|---|---|---|---|---|---|---|---|---|---|---|---|
| | | | | Butene[1] | O$_2$:N$_2$[2] | | | | MEK[4] | CO$_2$ | CO | SBA[5] | C$_4$SH[6] |
| 1 | 0.6 | 315 | 9.0 | 60 | 380 | 224 | 3984 | 11.8 | 65.3 | 22.7 | 3.4 | 1.3 | 4.1 |
| 2 | 2.7 | 301 | 9.5 | 104 | 730 | 224 | 6336 | 14.0 | 56.5 | 20.7 | 13.0 | 1.1 | 1.9 |

[1]Feed = gas mixture containing 85 vol. % butene-1 and 15 vol. % iso-butane.
[2]Fed as 10 vol. % O$_2$ in N$_2$
[3]Total gas hourly space velocity.
[4]Methyl ethyl ketone.
[5]Secondary butyl alcohol.
[6]Butyl mercaptan.

Fifteen cc. of the palladium-rhenium-molybdenum oxide catalyst prepared in Example 13 was further vacuum impregnated using the procedure of Example 1 with a 5.1 cc. aqueous solution containing 0.069 grams of sodium nitrate, followed by the four-step drying and calcining procedure employed in Example 13. The resulting solids were found to additionally contain 0.1 wt.% Na, calculated as the element, based on the weight of the total catalyst support in addition to the 1.08% Pd, 3.7% Re, and 9.5% Mo. This catalyst was then mixed with inerts and sulfided using the procedure set forth above in Example 3, and the resulting sulfided catalyst was then contacted with a butene gas as in Example 13 except that the reaction temperature was 304° C. and the gas inlet pressure was 9.4 psig. At a butene conversion of 10.8%, the following selectivities were observed: 39.8% methyl ethyl ketone, 2.8% secondary butyl alcohol, 13.5% CO$_2$ and 14.6% CO.

EXAMPLE 15

Following the procedure of Example 1, 26.4 grams of dry gamma-alumina was sequentially impregnated with Mo (using 10.6 cc. of an aqueous solution containing 4.62 grams of ammonium permolybdate), Re (using 10.3 cc. of an aqueous solution containing 1.42 grams of ammonium perrhenate), and finally by Rh (using 10.3 cc. of an aqueous solution containing 0.37 gram of rhodium trinitrate). After each impregnation, the solids are dried under air at 125° C. for 1 hour, 253° C. for 1 hour, and 350° C. for 1 hour, and then calcined under air at 500° for 3 hours. The resulting oxide catalyst was found to comprise 0.5 wt.% Rh, 3.7 wt.% Re, and 9.5 wt.% Mo, calculated as a respective element, based on the total weight of the support. The oxide catalyst was mixed with inerts and sulfided using the procedure of Example 3, and the resulting sulfided catalyst was employed in a series of runs using conditions set forth in Table IX.

EXAMPLE 16

The catalyst preparation procedure of Example 15 is repeated except that the catalyst solids, following the last calcining step, were then impregnated with 10.3 cc. of an aqueous solution containing 0.11 gram of sodium nitrate. These impregnated solids, containing 0.1 wt.% Na, 0.5 wt.% Rh, 3.7 wt.% Re and 9.5 wt.% Mo (calculated as metals, based on support) were then dried and calcined in air using the procedure of Example 15, and mixed with inerts and sulfided in the reactor employing the procedure of Example 3. Thereafter, the sulfided catalyst was used in a series of runs using the procedure of Example 1. Further data thereby obtained are set forth in Table X.

TABLE X

| Run No. | Time. (hrs) | Temp (°C.) | Press. psig | Gas Feed (cc/min.) | | H$_2$O Vapor | GHSV[3] (cc/cc/ hr) | Butene Conv. (%) | % Selectivities | | | | |
|---|---|---|---|---|---|---|---|---|---|---|---|---|---|
| | | | | Butene[1] | O$_2$:N$_2$[2] | | | | MEK[4] | CO$_2$ | CO | SBA[5] | C$_4$SH[6] |
| 1 | 0.7 | 285 | 9.1 | 60 | 380 | 224 | 3984 | 11.6 | 60.2 | 28.8 | 0 | 0.9 | 4.0 |
| 2 | 1.8 | 295 | 9.2 | 104 | 730 | 224 | 6336 | 14.5 | 46.3 | 22.8 | 12.0 | 0.3 | 4.6 |

[1]Feed = gas mixture containing 85 vol. % butene-1 and 15 vol. % iso-butane.
[2]Fed as 10 vol. % O$_2$ in N$_2$
[3]Total gas hourly space velocity.
[4]Methyl ethyl ketone.
[5]Secondary butyl alcohol.
[6]Butyl mercaptan.

EXAMPLE 17

The multi-step impregnation procedure of Example 13 above was repeated employing 12.4 grams of the dry gamma-alumina support. The first impregnation employed 5.5 cc. of an aqueous solution containing 2.17 grams of ammonium paramolybdate, followed by use of a 5.4 cc. aqueous solution containing 0.79 grams of ammonium perrhenate, and finally by an impregnation using 5.5 cc. of an aqueous solution containing 0.39 grams of rhodium trinitrate. The four-step drying and calcining procedure of Example 13 was used, and the resulting oxide catalyst was found to contain Rh, Re and Mo in an amount of 1.0 wt.%, 3.7 wt.% and 9.7 wt.%, calculated as the respective elements based on the catalyst support. These solids were mixed with inerts and tested using the procedure of Example 1. The data thereby obtained is set forth in Runs 1 and 2 of Table XI.

The catalyst employed in Run 2 was next sulfided using the procedure of Example 3 and the resulting sulfided trimetallic rhodium-rhenium-molybdenum catalyst was employed in Run 3 of Table XI.

TABLE XI

| Run No. | Time (hrs) | Temp. (°C.) | Press. psig | Gas Feed (cc/min.) Butene | Gas Feed (cc/min.) O$_2$:N$_2$[1] | H$_2$O Vapor | GHSV[2] (cc/cc/ hr) | Butene Conv. (%) | % Selectivities MEK[3] | CO$_2$ | CO | SBA[4] | C$_4$SH |
|---|---|---|---|---|---|---|---|---|---|---|---|---|---|
| | | | | | | Rh—Re—Mo Oxide | | | | | | | |
| 1 | 5.0 | 303 | 7 | 102 | 730 | 224 | 6338 | 29.8 | 68.9 | 12.9 | 11.6 | 1.4 | 0 |
| 2 | 8.3 | 304 | 7 | 60 | 380 | 224 | 3984 | 37.2 | 82.0 | 11.2 | 1.9 | 1.6 | 0 |
| | | | | | | Rh—Re—Mo Sulfide | | | | | | | |
| 3 | 1.5 | 305 | 7 | 60 | 380 | 224 | 3984 | 53.0 | 90.9 | 6.3 | 0 | 0 | 0 |

[1]Fed as 10 vol. % O$_2$ in N$_2$.
[2]Total gas hourly space velocity.
[3]Methyl ethyl ketone.
[4]Secondary butyl alcohol.

EXAMPLE 18 FOR COMPARISON

The procedure of Example 17 was repeated except that no rhenium was employed. The resulting oxide catalyst was found to comprise 1.0 wt.% Rh, and 9.5 wt.%, Mo, calculated as the elements, based on the weight of the gamma-alumina support. Runs A through C of Table XII employs this oxide catalyst. Runs D through F employed the corresponding rhodium-molybdenum sulfide catalyst prepared by sulfiding the catalyst after Run C, using the procedure of Example 3.

EXAMPLE 19

The catalyst procedure of Example 17 is repeated to provide a trimetallic oxide catalyst containing 1.0 wt.% Rh, 3.7 wt.% Re, and 9.5 wt.% Mo supported on gamma-alumina. This catalyst, after mixing with inerts, as in Example 1, is tested as in Example 17 at 302° C. employing a gas inlet pressure of about 8.5 psig and a gas feed comprising 60 cc./min. butene-1, 380 cc./min. O$_2$:N$_2$ (10:90 vol:vol mixture) and 224 cc./min. water vapor, for a total gas hourly space velocity of 3,984 cc/cc/hr., for a period of 9.5 hours. At a 42.9% butene conversion, the following selectivities were observed: methyl ethyl ketone 89.7%, secondary butyl alcohol 2.5%, and carbon dioxide 5.6%. No carbon monoxide by-product was detected.

The above catalyst was then sulfided using the procedure of Example 3 and employed in a separate run at 304° C. for a period of 13.0 hours, using the above process conditions. At a 47.6% butene conversion the following selectivities were observed: methyl ethyl ketone 88.4%, secondary butyl alcohol 3.7%, and carbon dioxide 6.0%. Again, no carbon monoxide by-product detected. In addition, no by-product butyl mercaptan was detected.

EXAMPLE 20

The procedure of Example 19 was repeated except that the Rh—Re—Mo on gamma-alumina catalyst thus prepared in oxide form was sulfided using the procedure of Example 3 prior to contacting this oxide solids with a butene-gas. After sulfiding, the catalyst, mixed with inerts, was contacted with a butene-1 feed employing the conditions set forth above for Example 19, except that a temperature of 298° C. was used and the run was continued for 1 hour. At a butene conversion of 44.5%, the following selectivities were observed: methyl ethyl ketone 86.6%, secondary butyl alcohol 3.2%, carbon dioxide 6.5%, and carbon monoxide 0.8%. In addition, secondary butyl mercaptan selectivity was 1.2%.

EXAMPLE 21

Gamma-alumina (30 cc.; 12–20 mesh) was dried using the procedure of Example 1 to a dry weight of 26.6 grams. A calculated amount of ammonium tetrathiomolybdate (6.85 grams of (NH$_4$)$_2$MoS$_4$) was dissolved in 61 cc. of distilled water and 11 cc. of the solution was employed in a first impregnation using the procedure of Example 1, followed by drying under helium at 125° C. for 1 hour, and 250° C. for 1 hour. Then the solids were allowed to cool to room temperature. The impregnation and drying procedure was then repeated five times, with each subsequent impregnation employing 10 cc. of the above solution.

After the sixth such impregnation and drying step, the dried solids, rather than being allowed to cool to room temperature, were calcined by raising the furnace temperature at a rate of about 10° C. per minute to 350° C., which was maintained for 3 hours, under helium. Then, after cooling of the solids, one-third of the solids

TABLE XII

| Run No. | Time (hrs) | Temp. (°C.) | Press. psig | Gas Feed (cc/min.) 1-Butene | Gas Feed (cc/min.) O$_2$/N$_2$[1] | H$_2$O Vapor | GHSV[2] (cc/cc/ hr) | Butene Conv. (%) | % Selectivities MEK[3] | CO$_2$ | CO | SBA[4] |
|---|---|---|---|---|---|---|---|---|---|---|---|---|
| | | | | | | Rh—Mo Oxide | | | | | | |
| A | 8.9 | 250 | 7 | 102 | 730 | 224 | 6338 | 7.9 | 48.7 | 29.7 | 7.8 | 5.9 |
| B | 5.9 | 312 | 7 | 102 | 730 | 224 | 6338 | 28.4 | 69.5 | 13.7 | 6.8 | 3.6 |
| C | 0.6 | 301 | 7 | 60 | 730 | 224 | 6084 | 29.4 | 43.8 | 20.9 | 18.2 | 2.5 |
| | | | | | | Rh—Mo Sulfide | | | | | | |
| D | 2.4 | 310 | 7 | 60 | 730 | 224 | 6084 | 46.9 | 58.6 | 12.7 | 6.2 | 0 |
| E | 4.2 | 300 | 7 | 31 | 380 | 112 | 3138 | 36.3 | 48.5 | 31.5 | 5.3 | 0 |
| F | 6.4 | 302 | 7 | 102 | 730 | 224 | 6338 | 18.3 | 48.1 | 26.2 | 8.5 | 0 |

[1]Fed as 10 vol. % O$_2$ in N$_2$.
[2]Total gas hourly space velocity.
[3]Methyl ethyl ketone.
[4]Secondary butyl alcohol.

was impregnated with a 3.7 cc. aqueous solution containing 0.39 grams of ammonium perrhenate, and 0.20 grams of rhodium trinitrate. After this simultaneous Re/Rh impregnation, the solids were dried over helium at 125° C. for 1 hour.

Ten cc. of these solids were then mixed with 20 cc. of fused ceramic inerts (12-20 mesh) which was then loaded into the test reactor and sulfided employing the procedure of Example 3 to ensure complete sulfiding of the catalyst. A series of runs was then conducted using the catalyst, employing the conditions set forth in Table XIII.

EXAMPLE 22

Employing the procedure of Example 17, 26.5 grams of dried gamma-alumina 12-20 mesh; 100 m²/gm. was sequentially impregnated with a 10.7 cc. aqueous solution containing 4.64 grams of ammonium paramolybdate, followed by impregnation twice with 10.7 of an aqueous solution containing 1.42 grams of ammonium perrhenate and then by 10.7 cc. of an aqueous solution containing 1.71 grams of rhodium trinitrate. After each impregnation, the fourstep drying and calcining procedure of Example 17 was repeated under air. The resulting catalyst was found to comprise 2.0 wt.% Rh, 7.4 wt.% Re, and 9.5 wt.% Mo, calculated as the respective metal, based on the total weight of the gamma-alumina support.

This catalyst (10 cc.) was then mixed with 20 cc. of fused ceramic inerts of 12-20 mesh sulfided using the procedure according to Example 3, and tested following the procedure of Example 1, and using the conditions set forth in Table XIV, providing the data set forth in that table.

TABLE XIII

| Run No. | Time (hrs) | Temp. (°C.) | Press. psig | Gas Feed (cc/min.) 1-Butene | Gas Feed (cc/min.) $O_2/N_2^{(1)}$ | Gas Feed (cc/min.) $H_2O$ | $GHSV^{(2)}$ (cc/cc hr) | Butene Conv. (%) | % Selectivities $MEK^{(3)}$ | % Selectivities $CO_2$ | % Selectivities CO | % Selectivities $SBA^{(4)}$ | % Selectivities $C_4SH^{(5)}$ |
|---|---|---|---|---|---|---|---|---|---|---|---|---|---|
| 1 | 4.7 | 350 | 9.0 | 60 | 380 | 224 | 3984 | 5.6 | 89.0 | 0 | 4.8 | 0.6 | 0 |
| 2 | 1.9 | 300 | 9.0 | 60 | 380 | 224 | 3984 | 7.6 | 88.3 | 0 | 3.8 | 2.6 | 0 |
| 3 | 1.3 | 255 | 9.0 | 60 | 380 | 224 | 3984 | 7.0 | 89.7 | 0 | 1.1 | 5.7 | 0 |

$^{(1)}$Fed as 10 vol. % $O_2$ in $N_2$.
$^{(2)}$Total gas hourly space velocity.
$^{(3)}$Methyl ethyl ketone.
$^{(4)}$Secondary butyl alcohol.
$^{(5)}$Butyl mercaptan.

TABLE XIV

| Run No. | Time. (hrs) | Temp (°C.) | Press. psig | Gas Feed (cc/min.) $Butene^{(1)}$ | Gas Feed (cc/min.) $O_2/N_2^{(2)}$ | Gas Feed (cc/min.) $H_2O$ | $GHSV^{(3)}$ (cc/cc/ hr) | Butene Conv. (%) | % Selectivities $MEK^{(4)}$ | % Selectivities $CO_2$ | % Selectivities CO | % Selectivities $SBA^{(5)}$ | % Selectivities $C_4SH^{(6)}$ |
|---|---|---|---|---|---|---|---|---|---|---|---|---|---|
| 1 | 1.8 | 300 | 9.2 | 60 | 380 | 224 | 3984 | 4.3 | 25.3 | 48.1 | 11.5 | 9.0 | 0 |
| 2 | 3.0 | 306 | 9.3 | 102 | 730 | 224 | 6336 | 6.1 | 23.0 | 48.5 | 17.6 | 2.8 | 0 |
| 3 | 4.0 | 296 | 9.2 | 60 | 380 | 224 | 3984 | 10.1 | 44.9 | 26.0 | 8.3 | 0 | 3.5 |
| 4 | 6.5 | 306 | 9.2 | 60 | 380 | 224 | 3984 | 11.3 | 52.3 | 25.9 | 7.1 | 0 | 3.9 |
| 5* | 0.6 | 302 | 9.2 | 60 | 380 | 224 | 3984 | 7.3 | 36.1 | 40.5 | 2.4 | 0 | 11.1 |

$^{(1)}$Feed = gas mixture containing 85 vol. % butene-1 and 15 vol. % iso-butane.
$^{(2)}$Fed as 10 vol. % $O_2$ in $N_2$
$^{(3)}$Total gas hourly space velocity.
$^{(4)}$Methyl ethyl ketone.
$^{(5)}$Secondary butyl alcohol.
$^{(6)}$Butyl mercaptan.
*A separate catalyst charge, which was formed using the preparation used for the catalyst in Runs 1-4, except that a temperature of 375° C. was used in the sulfiding/$H_2$ stripping step of Example 3.

EXAMPLE 23

The catalyst preparation procedure of Example 17 was repeated employing 12.95 grams of dry gamma-alumina (12-20 mesh; 100 m²/gm.) in two impregnations; the first using a 5.3 cc. aqueous solution containing 1.16 grams of ammonium paramolybdate; and the second using a 5.3 cc. aqueous solution containing .035 gram of ammonium perrhenate and 0.18 grams of rhodium trinitrate. After each vacuum impregnation, the inter-stage, four-stage drying/calcining procedure of Example 17 was repeated, under $N_2$ (after the first impregnation) and air for the subsequent impregnation. The resulting oxide catalyst was found to contain 0.5 wt.% Rh, 1.85 wt.% Re, and 4.75 wt.% Mo, calculated as the respective elements, based on the weight of the gamma-alumina support. After mixing this oxide catalyst with inerts as in Example 17, the catalyst was subjected to the in situ sulfiding procedure of Example 3 and then tested as in Example 1, providing the data summarized in Table XV.

TABLE XV

| Run No. | Time. (hrs) | Temp (°C.) | Press. psig | Gas Feed (cc/min.) $Butene^{(1)}$ | Gas Feed (cc/min.) $O_2:N_2^{(2)}$ | Gas Feed (cc/min.) $H_2O$ | $GHSV^{(3)}$ (cc/cc/ hr) | Butene Conv. (%) | % Selectivities $MEK^{(4)}$ | % Selectivities $CO_2$ | % Selectivities CO | % Selectivities $SBA^{(5)}$ | % Selectivities $C_4S^{(6)}$ |
|---|---|---|---|---|---|---|---|---|---|---|---|---|---|
| 1 | 26.7 | 307 | 8.8 | 60 | 380 | 224 | 3984 | 4.6 | 38.9 | 42.9 | 10.7 | 3.3 | 0 |
| 2 | 27.3 | 309 | 8.7 | 30 | 170 | 224 | 2568 | 4.1 | 50.0 | 43.2 | 0 | 3.8 | 0 |

$^{(1)}$Feed = gas mixture containing 85 vol. % butene-1 and 15 vol. % iso-butane.
$^{(2)}$Fed as 10 vol. % $O_2$ in $N_2$.
$^{(3)}$Total gas hourly space velocity.
$^{(4)}$Methyl ethyl ketone.
$^{(5)}$Secondary butyl alcohol.
$^{(6)}$Butyl mercaptan.

EXAMPLE 24

The catalyst preparation procedure of Example 23 was repeated except that 12.9 gm of the dry gamma-alumina was used and the stepwise impregnation employed 6.2 cc. of an aqueous solution containing ammonium paramolybdate (2.25 grams), followed by 5.5 cc. of an aqueous solution containing 0.35 gram of ammonium perrhenate, and then by a 5.0 cc. of an aqueous solution containing 0.18 gram of rhodium trinitrate, again using the inter-stage, four-step drying/calcining procedure described in Example 17. The resulting oxide catalyst was found to contain 0.5 wt.% Rh, 1.8 wt.% Re, and 9.5 wt.% Mo, calculated as the elements, based on the weight of the gamma-alumina support. This oxide catalyst was then mixed with inerts as in Example 17, sulfided as in Example 3, and employed in a test reactor with a butene-feed, using the procedure of Example 1. The data obtained are set forth in Run 1 of Table XVI.

The catalyst in the reactor was then subjected to a sulfiding, using the procedure of Example 3 and subjected to three additional runs which are summarized in Table XVI.

velocity of 3,984 cc/cc/min. at a 8.0% butene conversion, the following selectivities were observed: methyl ethyl ketone 55.6%, secondary butyl alcohol 11.7%, carbon dioxide 16.9% and carbon monoxide 3.2%. In addition, 0.5% of butyl mercaptan was detected.

This catalyst was then subjected to an in situ sulfiding using the procedure of Example 3, and then tested in a separate run at 300° C. and a gas inlet pressure of 8.8 psig for 1.5 hours, using the same gas feed composition. At a butene conversion of 11.0%, the following selectivities were observed: methyl ethyl ketone 49.7%, carbon dioxide 23.4%, carbon monoxide 4.5% and butyl mercaptan 3.8%. No secondary butyl alcohol was detected.

EXAMPLE 26

The catalyst preparation procedure of Example 21 was repeated except that 15 cc. of the dried gamma-alumina solids were subjected to ten successive impregnations, each using 5.8 cc. of an aqueous solution containing 0.33 grams of ammonium tetrathiomolybdate, with each such impregnation being followed by drying at 125° C. for 1 hour in a vacuum oven (at a pressure of −30 inches of mercury). After the tenth impregnation,

TABLE XVI

| Run No. | Time (hrs) | Temp. (°C.) | Press. psig | Gas Feed (cc/min.) 1-Butene | $O_2/N_2$[1] | $H_2O$ | GHSV[2] (cc/cc/hr) | Butene Conv. (%) | % Selectivities MEK[3] | $CO_2$ | CO | SBA[4] | $C_4SH$[5] |
|---|---|---|---|---|---|---|---|---|---|---|---|---|---|
| 1 | 1.0 | 322 | 9.0 | 60 | 380 | 224 | 3984 | 5.6 | 77.6 | 15.9 | 4.5 | 0 | 0 |
| 2 | 1.0 | 292 | 8.8 | 60 | 380 | 224 | 3984 | 8.8 | 59.6 | 23.9 | 6.5 | 0 | 1.4 |
| 3 | 1.3 | 298 | 8.8 | 60 | 380 | 224 | 3984 | 8.8 | 60.6 | 23.9 | 6.5 | 0 | 1.2 |
| 4 | 3.7 | 392 | 9.0 | 60 | 380 | 224 | 3984 | 13.8 | 66.6 | 18.8 | 6.3 | 0 | 1.9 |

[1]Fed as 10 vol. % $O_2$ in $N_2$.
[2]Total gas hourly space velocity.
[3]Methyl ethyl ketone.
[4]Secondary butyl alcohol.
[5]Butyl mercaptan.

EXAMPLE 25

The catalyst prepartion procedure of Example 17 was repeated except that the dried support comprised 11.4 grams of dry gamma-alumina (12–20 mesh; 200 m²/gm surface area; 0.50 cc/gm. pore volume; Strem Chemical). The catalyst thus-produced contained the same loading of rhodium, rhenium and molybdenum employed in the catalyst of Example 17. After mixing 10 cc. of this oxide catalyst with 20 cc. of fused ceramic inerts (12–20 mesh), the catalyst was tested as in Example 17 at 302° C. and gas inlet pressure of 9.0 psig for 0.8 hour, using a gas feed comprising 60 cc./min. butene-1, 380 cc./min. $O_2:N_2$ (10:90 vol:vol gas mixture) and 224 cc./min. of water vapor, for a total gas hourly space the solids were dried in a Linberg furnace at 250° C. under helium for 2 hours, followed by allowing the solids to cool, and a vacuum impregnation using 6.0 cc. of an aqueous solution containing 0.694 grams of ammonium perrhenate and 0.36 gram of $Rh(NO_3)_3$. After drying of these solids in the vacuum oven at 125° C. for 1 hour, the solids were dried in the Linberg furnace at 250° C. for 2 hours under helium and the solids were then mixed with inerts and sulfided using the procedure of Example 3.

A long-term test of these sulfided catalysts, which was found to comprise 1.08 wt.% Rh, 3.7 wt.% Re, and 9.5 wt.% Mo, was then made using the procedure of Example 1. The results were set forth in Table XVII.

TABLE XVII

| Run No. | Time (hrs) | Temp. (°C.) | Press. psig | Gas Feed (cc/min.) 1-Butene | $O_2/N_2$[1] | $H_2O$ | GHSV[2] | Butene Conv. (%) | % Selectivities MEK[3] | $CO_2$ | CO | SBA[4] | $C_4SH$[5] |
|---|---|---|---|---|---|---|---|---|---|---|---|---|---|
| 1 | 1.5 | 296 | 63 | 8.5 | 380 | 224 | 3984 | 27.8 | 81.6 | 12.7 | 0.9 | 2.5 | 0.3 |
| 2 | 2.5 | 310 | 63 | 8.5 | 380 | 224 | 3984 | 28.6 | 75.9 | 12.0 | 2.8 | 3.9 | 0.5 |
| 3 | 3.0 | 301 | 63 | 8.5 | 380 | 224 | 3984 | 30.1 | 78.4 | 11.2 | 2.2 | 4.1 | 0.4 |
| 4 | 6.0 | 298 | 63 | 8.5 | 380 | 224 | 3984 | 27.6 | 72.5 | 13.5 | 2.5 | 4.3 | 0.3 |
| 5 | 6.5 | 296 | 63 | 8.5 | 380 | 224 | 3984 | 27.6 | 72.5 | 13.0 | 2.5 | 3.2 | 0.5 |
| 6 | 7.5 | 300 | 62 | 8.5 | 380 | 224 | 3984 | 27.2 | 76.5 | 12.0 | 2.4 | 2.4 | 0.4 |
| 7 | 10.0 | 308 | 62 | 8.5 | 380 | 224 | 3984 | 27.2 | 80.0 | 11.1 | 1.4 | 3.4 | 1.2 |
| 8 | 22.8 | 299 | 62 | 8.5 | 380 | 224 | 3984 | 31.1 | 76.6 | 10.5 | 1.8 | 6.6 | 0 |

TABLE XVII-continued

| Run No. | Time (hrs) | Temp. (°C.) | Press. psig | Gas Feed (cc/min.) | | | | Butene Conv. (%) | % Selectivities | | | | |
|---|---|---|---|---|---|---|---|---|---|---|---|---|---|
| | | | | 1-Butene | $O_2/N_2$[1] | $H_2O$ | GHSV[2] | | MEK[3] | $CO_2$ | CO | SBA[4] | $C_4SH$[5] |
| 9 | 23.3 | 304 | 62 | 8.5 | 380 | 224 | 3984 | 28.0 | 74.0 | 11.8 | 1.9 | 6.7 | 0 |

[1]Fed as 10 vol. % $O_2$ in $N_2$.
[2]Total gas hourly space velocity.
[3]Methyl ethyl ketone.
[4]Secondary butyl alcohol.
[5]Butyl mercaptan.

EXAMPLE 27

The multi-step impregnation procedure of Example 17 above was repeated except that the support in this experiment comprised 5.37 grams (after the drying step) of silica-alumina (Davison Chemical Company, silica-alumina No. 979; 86.0% silica, 13% alumina; 400 m$^2$/gm.; 1.16 cc./gm. pore volume; 12–20 mesh In the first impregnation, a 6.2 cc. aqueous solution containing 0.94 gram of ammonium paramolybdate was used, followed by the four-step drying/calcining procedure of Example 17. The second impregnation employed a 6.2 cc. aqueous solution containing 0.29 gram of ammonium perrhenate and the third impregnation used 6.2 cc. of an aqueous solution containing 0.15 gram of ammonium nitrate. The same drying/calcining procedure was also used after each of the last two impregnations.

Ten cc. of the above oxide solids, which were found to contain 1.08 wt.% Rh, 3.7 wt.% Re and 9.5 wt.% Mo, calculated as the respective metals, based on the weight of the total silica-alumina support, was mixed with 20 cc. of 12–20 mesh fused ceramic inerts and charged to the reactor for testing as in Example 1. The data thereby obtained are set forth in Runs 1 and 2 of Table XVIII.

At the end of Run 2, the catalyst was subjected to sulfiding employing the procedure of Example 3, except that the passage of the H$_2$S gas was continued for 1 hour and the hydrogen stripping step was carried out for only one-half hour. At the end of this time, the butene-feed was resumed and the catalyst employed in Run 3 of Table XVIII.

the four-step drying/calcining procedure of Example 17 was repeated. The resulting oxide catalyst was found to contain 1.0 wt.% Rh, 3.7 wt.% Re, and 9.5 wt.% Mo, calculated as the metals, based on the weight of the silica gel support. Ten cc. of this oxide catalyst was then well mixed with 20 cc. of 12–20 mesh fused ceramic inerts and charged to the reactor and sulfided as in Example 3 followed by testing using the procedure of Example 1.

The reactor was maintained at a temperature of 310° C. and a gas inlet pressure of 8.8 psig, for 0.8 hour. The gas feed to the reactor comprised 102 cc./min. of a gas mixture containing 85 vol.% butene-1, 15 vol.% n-butane, 730 cc./min. of an oxygen-containing gas mixture (10 vol.% oxygen in nitrogen) and 224 cc./min. of water vapor, for a total gas hourly space velocity of 6336 cc/cc/hr. At a butene conversion of 5.5%, methyl ethyl ketone was formed only in a selectivity of 0.7% and carbon dioxide selectivity was observed to be 16.7%, with a 63.3% selectivity to carbon monoxide. In view of the low ketone selectivity obtained under the above conditions, silica gel is not a preferred catalyst support for use in the practice of this invention.

EXAMPLE 29

Using the procedure as described above for Example 1(a), 15 cc. of the gamma-alumina (12–20 mesh) was dried in air at 500° C. for 3 hours, to provide a dry weight of 13.4 grams. Ammonium tungstate (1.753 grams, (NH$_4$)$_{10}$W$_{12}$O$_4$.5H$_2$O) was dissolved in water to make a 27 cc. solution, which was observed to contain some undissolved solids. In a first impregnation, approximately 5.3 cc. of this aqueous solution was impregnated onto the dried solid, after which the impregnated solids were dried in air at 125° C. for 1 hour followed by 250° C. for 1 hour. This procedure was repeated 3 times, and a total of 0.36 gram of insoluble ammonium tungstate was recovered following the last impregnation, to provide a net of 1.39 grams of ammonium tungstate impregnated onto the support. The above two-step drying procedure was used after each of the successive impregnations, except that after the fifth such impregnation the catalyst was additionally dried at 350° C. for 1 hour, followed by calcining at 500° C. for 3 hours, in air.

TABLE XVIII

| Run No. | Time (hrs) | Temp. (°C.) | Press. psig | Gas Feed (cc/min.) | | | | Butene Conv. (%) | % Selectivities | | | | |
|---|---|---|---|---|---|---|---|---|---|---|---|---|---|
| | | | | Butene[1] | $O_2/N_2$[2] | $H_2O$ | GHSV[3] | | MEK[4] | $CO_2$ | CO | SBA[5] | $C_4SH$[6] |
| 1 | 0.6 | 296 | 9.2 | 60 | 380 | 224 | 3984 | 7.1 | 13.2 | 32.4 | 29.4 | 3.4 | 0.3 |
| 2 | 2.0 | 295 | 9.2 | 102 | 730 | 224 | 6336 | 8.0 | 12.2 | 26.3 | 42.5 | 2.1 | 0.8 |
| 3 | 3.0 | 304 | 9.2 | 60 | 380 | 224 | 3984 | 4.9 | 13.6 | 31.7 | 38.3 | 2.0 | 1.0 |

[1]Feed = gas mixture containing 85 vol. % d butene-1 and 15 vol. % iso-butane.
[2]Fed as 10 vol. % $O_2$ in $N_2$.
[3]Total gas hourly space velocity.
[4]Methyl ethyl ketone.
[5]Secondary butyl alcohol.
[6]Butyl mercaptan.

EXAMPLE 28

The procedure of Example 27 was repeated except that the support comprised 5.34 grams (prepared by drying 15.0 cc. of support at 500° C. for 3 hours in air) of silica gel (Strem Chemical; 12–20 mesh; 340 m$^2$/gm.; 1.18 cc./gm, pore volume). The sequential impregnation employed the following amounts of the indicated solutions; 6.3 cc. of an aqueous solution containing 0.93 gram of ammonium paramolybdate; 6.3 cc. of an aqueous solution containing 0.29 gram of ammonium perrhenate; and 6.3 cc. of an aqueous solution containing 9.16 gram of rhodium trinitrate. After each impregnation, In a subsequent impregnation, 5.4 cc. of an aqueous solution containing 0.58 grams of ammonium perrhenate were impregnated onto the catalyst, followed by drying at 125° C. for 1 hour, 202° C. for 1 hour, and 350° C. for 1 hour, and calcining at 500° C. for 3 hours, in air. The resulting oxide catalyst was found to contain 3.0 wt.% rhenium and 7.5 wt.% tungsten, calculated as the elements, based on the weight of the catalyst support. Ten cc. of the resulting catalyst was then mixed with 20 cc. of fused ceramic inerts (12–20 mesh) and tested as in Example 3, at the conditions summarized in Table XIX, Run 1 below.

The oxide catalyst used in Run 1 was then sulfided using the procedure of Example 3, after which the sulfided catalyst was employed in Run 2, using the conditions described in Table XIX.

containing 1.63 grams of ammonium perrhenate, to prepare a sulfided Re—Mo catalyst, supported on gamma-alumina, comprising 3.7 wt.% Re and 9.5 wt.% Mo, calculated as the respective elements. The catalyst was then used in a series of runs over extended time periods. The data thereby obtained is set forth in Table XX below.

TABLE XX

| Run No. | Time (hrs) | Temp. (°C.) | Press. (psig) | Gas Feed (cc/min.) Butene[1] | $O_2/N_2$[1] | $N_2$[2] | $H_2O$ | GHSV[3] | Butene Conv. (%) | % Selectivities MEK[4] | $CO_2$ | CO | SBA[5] | Others |
|---|---|---|---|---|---|---|---|---|---|---|---|---|---|---|
| 1 | 10.7 | 372 | 8.0 | 60 | 60 | 320 | 224 | 3984 | 2.5 | 69.7 | 3.8 | 0 | 0.5 | 26.0 |
| 2 | 11.9 | 384 | 9.0 | 60 | 30 | 350 | 224 | 3984 | 2.8 | 90.2 | 3.0 | 0 | 0.4 | 6.4 |
| 3 | 14.0 | 384 | 9.0 | 60 | 30 | 0 | 224 | 1884 | 2.3 | 91.1 | 4.8 | 0 | 0.8 | 2.0 |

[1]Feed = Gas mixture containing 85 vol. % butene-1 and 15 vol. % iso-butane.
[2]Fed as 10 vol. % $O_2$ in $N_2$.
[3]Total gas hourly space velocity.
[4]Methyl ethyl ketone.
[5]Secondary butyl alcohol.

EXAMPLE 31

The procedure of Example 20 was repeated employing the sulfided Rh-Re-Mo on gamma-alumina catalyst of that example, except that the feed olefin comprised cyclohexene and the conditions of the test were as identified in Table XXI below. A series of runs were conducted in which the reaction temperature was varied, indicating the higher selectivities of cyclohexanone obtained at temperatures of less than about 220° C.

TABLE XIX

| Run No. | Time (hrs) | Temp. (°C.) | Press. psig | Gas Feed (cc/min.) Butene[1] | $O_2/N_2$[2] | $H_2O$ | GHSV[3] | Butene Conv. (%) | % Selectivities MEK[4] | $CO_2$ | CO | SBA[5] |
|---|---|---|---|---|---|---|---|---|---|---|---|---|
| | | | | | Re—W Oxide | | | | | | | |
| 1 | 2.3 | 313 | 9.4 | 60 | 380 | 224 | 3984 | 5.1 | 51.0 | 3.1 | 4.7 | 34.5 |
| | | | | | Re—W Sulfide | | | | | | | |
| 2 | 2.5 | 299 | 9.7 | 60 | 380 | 224 | 3984 | 2.1 | 40.5 | 3.8 | 7.7 | 31.0 |

[1]Feed = Gas mixture containing 85 vol. % butene-1 and 15 vol. % iso-butane.
[2]Fed as 10 vol. % $O_2$ in $N_2$.
[3]Total gas hourly space velocity.
[4]Methyl ethyl ketone.
[5]Secondary butyl alcohol.

TABLE XXI

| Run No. | Time (hrs) | Temp. (°C.) | Press. psig | Gas Feed (cc/min.) Cyclohexene | Air[1] | $N_2$ | $H_2O$ | GHSV[2] | Cyclohexene Conv. (%) | % Selectivities Cyclohexanone | $CO_2$ | Cyclohexanol |
|---|---|---|---|---|---|---|---|---|---|---|---|---|
| 1 | 1.75 | 267 | 18 | 88 | 173 | 0 | 231 | 2952 | 3.0 | 2–5 | >80 | N.D. |
| 2 | 0.25 | 216 | 18 | 60 | 83 | 83 | 216 | 2652 | 0.51 | 33.3 | N.D. | 11.8 |
| 3 | 0.50 | 145 | 18 | 54 | 83 | 83 | 220 | 2640 | 1.65 | 12.7 | N.D. | 63.6 |
| 4 | 0.75 | 153 | 18 | 84 | 83 | 83 | 212 | 2772 | 0.64 | 9.4 | N.D. | 35.9 |
| 5 | 1.00 | 150 | 18 | 82 | 83 | 83 | 220 | 2808 | 0.37 | 8.1 | N.D. | 21.6 |
| 6 | 1.25 | 162 | 18 | 70 | 83 | 83 | 187 | 2538 | 0.32 | 6.3 | N.D. | 18.8 |
| 7 | 1.58 | 205 | 75 | 58 | 83 | 83 | 183 | 2442 | 13.6 | 7.9 | 41.5 | 1.3 |
| 8 | 1.83 | 196 | 75 | 77 | 83 | 83 | 332 | 3450 | 14.0 | 8.1 | 40.3 | 0.9 |
| 9 | 2.08 | 210 | 75 | 76 | 83 | 83 | 257 | 2994 | 25.1 | 19.0 | 22.5 | 0.6 |

[1]At 10 vol. % $O_2$ (air diluted with $N_2$).
[2]Gas hourly space velocity (cc/cc/hr.).
(N.D. = Not determined)

EXAMPLE 30

The catalyst preparation and sulfiding procedure of Example 15 was repeated (except that no Rh salt was employed), using 37 cc of gamma-alumina and 12.0 cc of an aqueous solution containing 5.24 grams of ammonium paramolybdate and 12.0 cc of an aqueous solution

EXAMPLE 32

The procedure of Example 31 was repeated using the Rh-Re-Mo sulfided catalyst of that example, except that the olefin feed comprised hexene-1, and the conditions employed were as summarized in Table XXII below.

TABLE XXII

| Run No. | Time (hrs) | Temp. (°C.) | Press. psig | Gas Feed (cc/min.) Air[1] | H$_2$O | n-hexene-1 | GHSV[2] | n-hexene Conv. (%) | % Selectivities CO$_2$ | hexanone-2 | unidentified[3] |
|---|---|---|---|---|---|---|---|---|---|---|---|
| 1 | .25 | 317 | 18 | 158 | 158 | 64 | 2280 | 12.6 | 34.0 | 0.6 | 60.5 |
| 2 | 0.75 | 304 | 18 | 158 | 149 | 82 | 2334 | 9.1 | 47.1 | 0.5 | 49.8 |
| 3 | 1.00 | 303 | 18 | 158 | 158 | 60 | 2256 | 9.3 | 46.3 | 0.9 | 50.1 |

[1]Air contains 20 vol. % oxygen.
[2]Gas hourly space velocity (cc/cc/hr.).
[3]An unidentified major peak, eluting prior to hexanone-2 on the GC trace, was observed, and is believed to have contained significant amounts of hexanone-3, formed from a large amount of hexene-2 and hexene-3 which result from the rapid thermal equilibrium established between the isomers of hexene in the reactor.

In each of the foregoing examples illustrative of the process of this invention, butane by-product was observed to be formed from the butene feeds in selectivities of less than about 0.5 mol.%, based on the butene fed to the reactor. Thus, the improved process of this invention allows the formation of the desired ketone in the substantial absence of olefin hydrogenation by-products, that is, the hydrogenation by-products will be generally formed in a selectivity of less than about 1 mol.%, based on the olefin fed.

Preferably, monoolefin feeds to the process of this invention are substantially free (e.g., contain less than 1 wt.%) of diolefins or acetylenic hydrocarbons to obtain the highest catalyst activity to form the ketones corresponding to the monoolefin feeds.

It will be obvious that various changes and modifications may be made without departing from the invention and it is intended, therefore, that all matter contained in the foregoing description shall be interpreted as illustrative only and not limitative of the invention.

What is claimed is:

1. A process for preparing ketones which comprises contacting the corresponding olefin in the gaseous phase with water vapor and molecular oxygen in a reaction zone at elevated temperature in the presence of a catalyst comprising rhenium sulfide, said olefin comprising at least one member selected from the group consisting of linear mono-olefins of from 2 to 20 carbon atoms and cyclic mono-olefins of from 3 to 20 carbon atoms.

2. The process according to claim 1 wherein said catalyst additionally comprises at least one promoter selected from the group consisting of sulfides of Group VIB and Group VIII noble metals.

3. The process according to claim 1 wherein said catalyst comprises a mixture of (1) a sulfide of Re, (2) a sulfide of Cr, Mo or W, and (3) a sulfide of Ru, Rh, Pd, Os, Ir or Pt.

4. The phase process according to claim 1 wherein said olefin comprises an alkene of from 4 to 10 carbon atoms or a cycloalkene of from 4 to 10 carbon atoms.

5. A process for preparing an alkanone of from 4 to 10 carbon atoms which comprises contacting the corresponding alkene having from 4 to 10 carbon atoms with water vapor and molecular oxygen in the presence of a catalyst comprising a compound or complex of rhenium.

6. The process according to claim 1 wherein the catalyst is supported on gamma-alumina.

7. A process for converting an olefin selected from the group consisting of alkenes having from 4 to 10 carbon atoms and cycloalkenes having from 4 to 10 carbon atoms into the corresponding ketone, which comprises contacting said olefin in the gaseous phase with water vapor and molecular oxygen in a reaction zone in the presence of a solid catalyst comprising rhenium sulfide, at a temperature of from about 125° to 600° C. and at pressures of from about 0 to 2000 psig.

8. The process according to claim 7 wherein said water vapor and said olefin are introduced into said reaction zone in a molar ratio of olefin:water vapor of from about 2:1 to 1:20.

9. The process according to claim 7 wherein said catalyst additionally comprises at least one promotor selected from the group consisting of sulfides of Cr, Mo, W, Ru, Rh, Pd, Os, Ir and Pt.

10. The process according to claim 8 wherein said temperature is from 200° to 400° C., and said olefin and water vapor are contacted at a gas hourly space velocity through the reaction zone of from 100 to 10,000 v/v/hour.

11. The process according to claim 8 wherein said olefin comprises butene-1 and said ketone comprises methyl ethyl ketone.

* * * * *